(12) United States Patent  
Berger

(10) Patent No.: US 8,529,260 B2
(45) Date of Patent: Sep. 10, 2013

(54) DENTURE STABILIZATION SYSTEM AND METHOD

(75) Inventor: Uzi Berger, Hod Hasharon (IL)

(73) Assignee: Kamil Tech Ltd., Road Town, Tortola (VG)

(*) Notice: Subject to any disclaimer, the term of this patent is extended or adjusted under 35 U.S.C. 154(b) by 0 days.

(21) Appl. No.: 12/903,607

(22) Filed: Oct. 13, 2010

(65) Prior Publication Data

US 2012/0094253 A1   Apr. 19, 2012

(51) Int. Cl.
*A61C 8/00* (2006.01)
*A61C 13/12* (2006.01)

(52) U.S. Cl.
USPC ............................. 433/172; 433/173; 433/174

(58) Field of Classification Search
USPC .............. 433/167–176, 201.1, 181–182, 215; 264/16–20
See application file for complete search history.

(56) References Cited

U.S. PATENT DOCUMENTS

| | | | | |
|---|---|---|---|---|
| 2,803,060 | A | * | 8/1957 | Weiss ............................. 433/177 |
| 4,085,506 | A | | 4/1978 | Lew |
| 4,203,216 | A | | 5/1980 | Deguemp |
| 4,715,817 | A | * | 12/1987 | Zuest et al. .................... 433/181 |
| 4,741,698 | A | | 5/1988 | Andrews |
| 4,904,186 | A | * | 2/1990 | Mays ............................ 433/172 |
| 4,931,016 | A | * | 6/1990 | Sillard ........................... 433/172 |
| 5,013,243 | A | | 5/1991 | Tanaka et al. |
| 5,057,017 | A | * | 10/1991 | Sillard ........................... 433/172 |
| 5,503,557 | A | | 4/1996 | Sillard |
| 7,806,691 | B2 | * | 10/2010 | Berger .......................... 433/172 |
| 2003/0187510 | A1 | | 10/2003 | Hyde |
| 2006/0223029 | A1 | * | 10/2006 | Berger .......................... 433/172 |
| 2008/0199824 | A1 | | 8/2008 | Hargadon |
| 2008/0280255 | A1 | * | 11/2008 | D'Alise ........................ 433/174 |

FOREIGN PATENT DOCUMENTS

| | | |
|---|---|---|
| WO | 82/03547 A1 | 10/1982 |
| WO | 2006/103648 A1 | 10/2006 |

OTHER PUBLICATIONS

The International Search Report for International Application No. PCT/IL2011/000759, three pages, mailed on Mar. 6, 2012.

* cited by examiner

*Primary Examiner* — Yogesh Patel
(74) *Attorney, Agent, or Firm* — Vorys, Sater, Seymour and Pease LLP; Susanne M. Hopkins; William L. Klima

(57) ABSTRACT

A removable denture system comprising a personalized support beam fixedly attached to an individual's alveolar ridge above the mucous membrane by a plurality of dental implants; a personalized denture conforming with dental parameters of the individual and having fixedly integrated within a bottom surface thereof a super-structure having a cross-section conforming with that of the support beam; and a denture locking arrangement for securely locking and unlocking the denture to the support beam, at substantial zero tolerance therebetween, and wherein one of the support beam and the super-structure is configured with one or more positioning grooves extending parallel to a path of insert (POI) of the denture, and the other of the support beam and the super-structure is configured with corresponding one or more laterally projecting positioning projections, each extending in register with a corresponding positioning grove and configured for snug sliding there within.

46 Claims, 18 Drawing Sheets

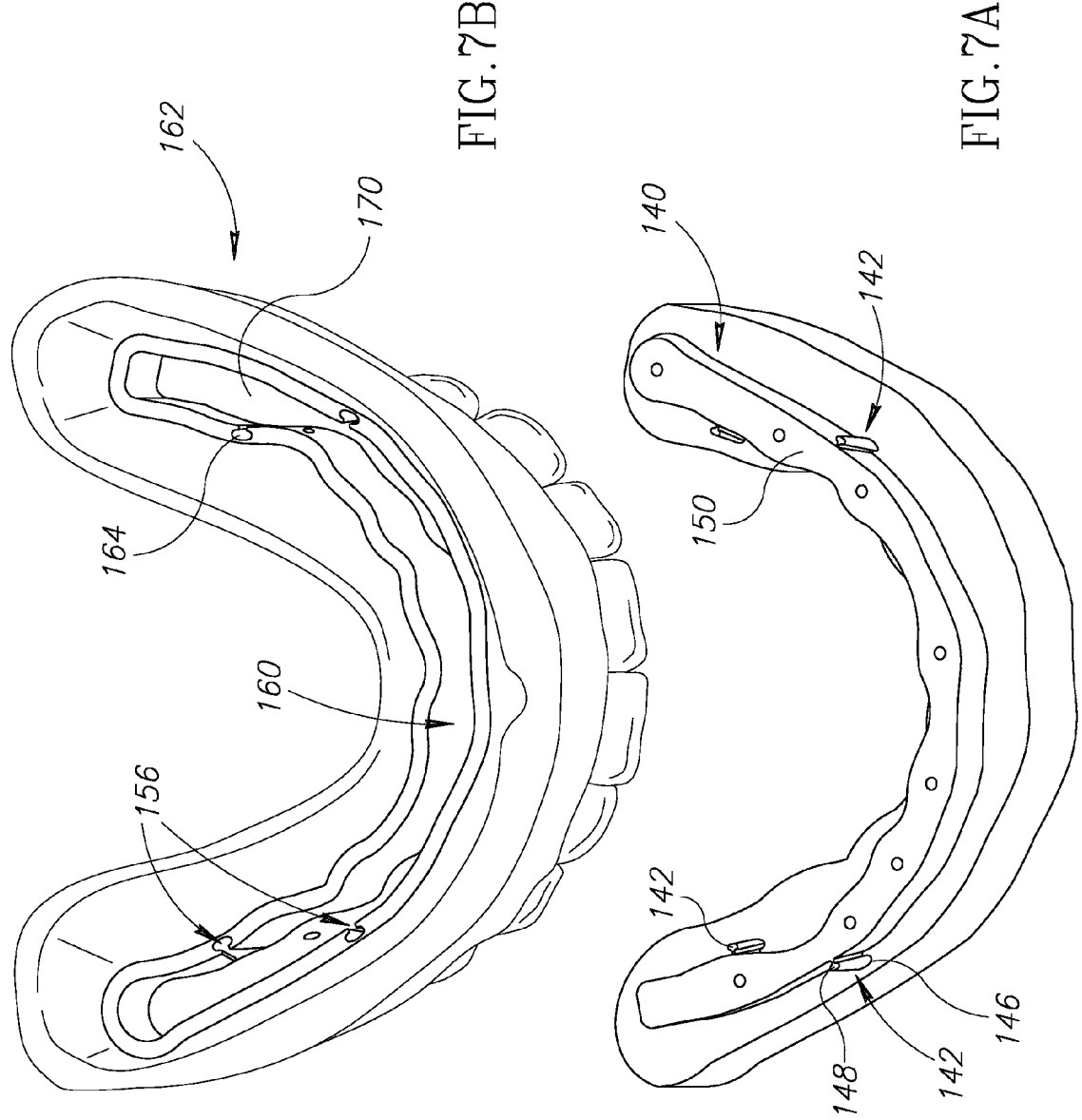

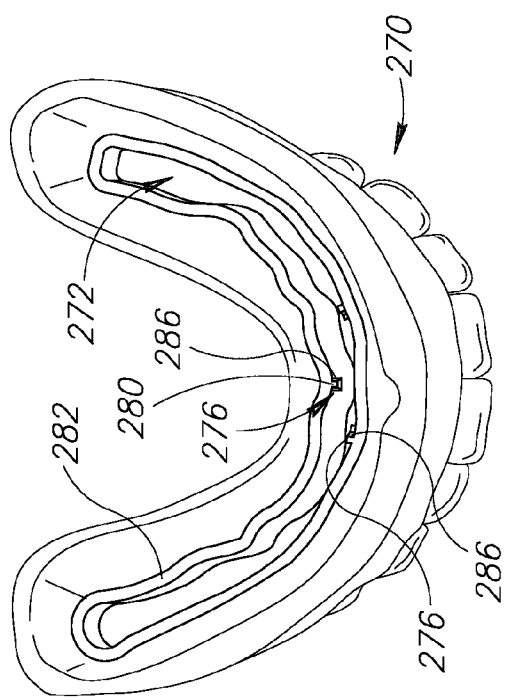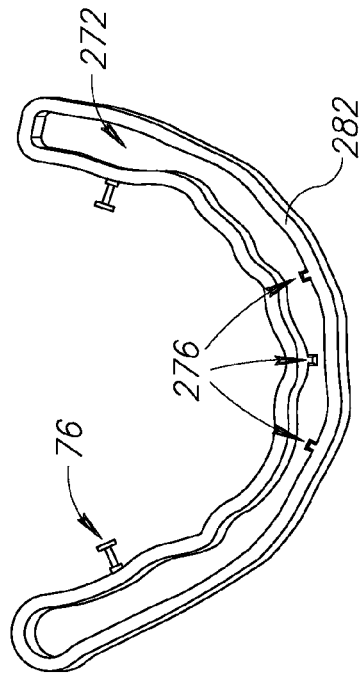
FIG.12A
FIG.12B
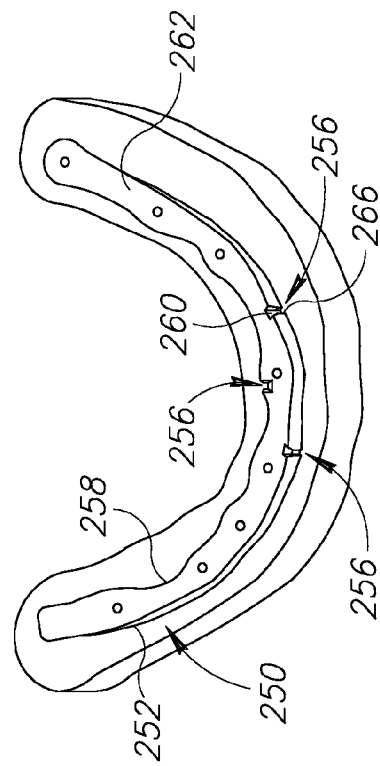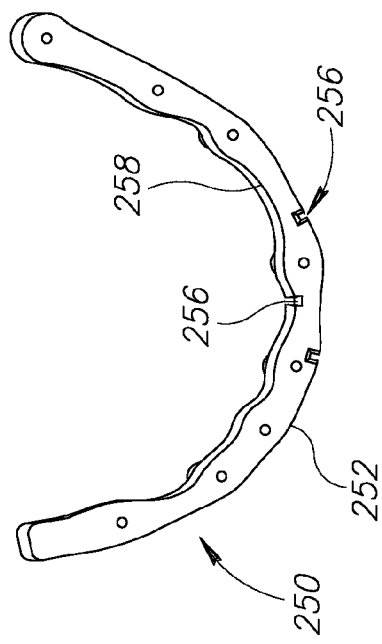
FIG.11A
FIG.11B

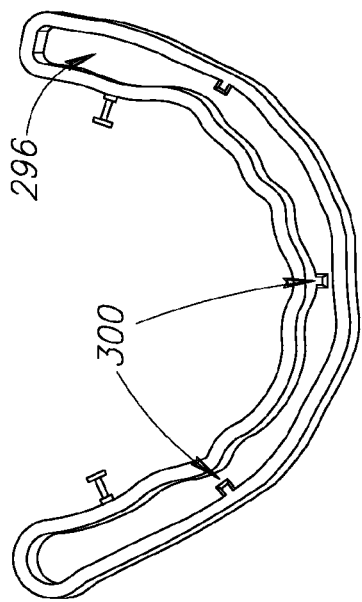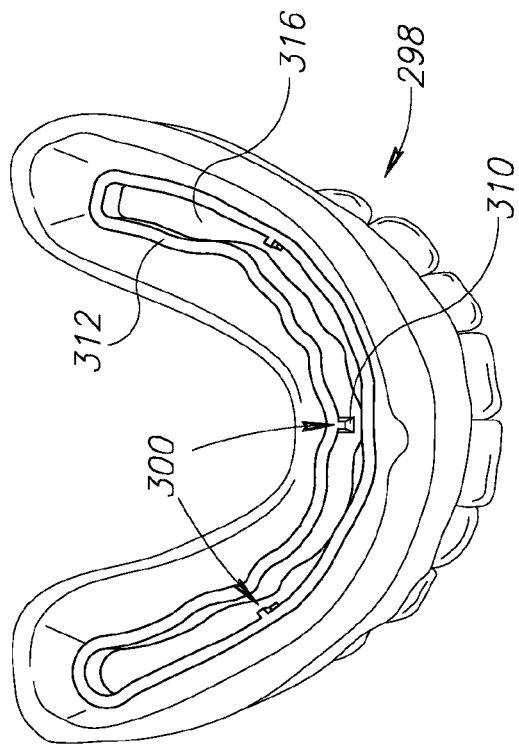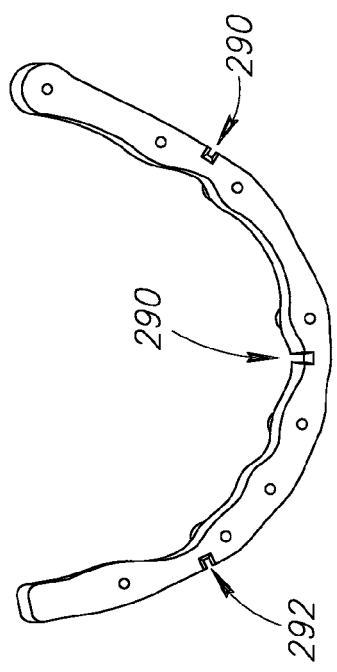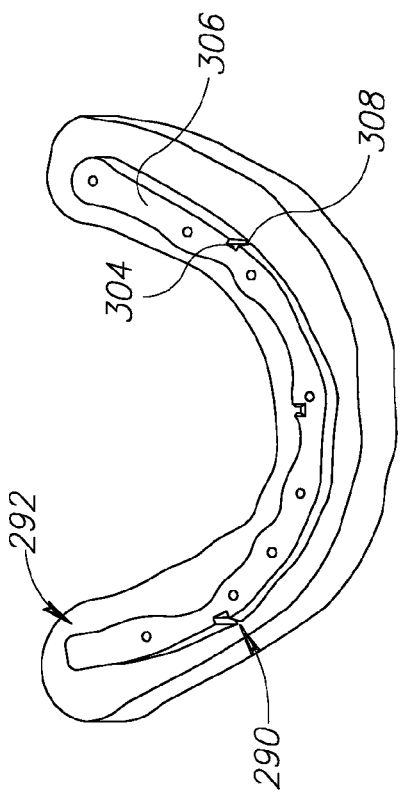

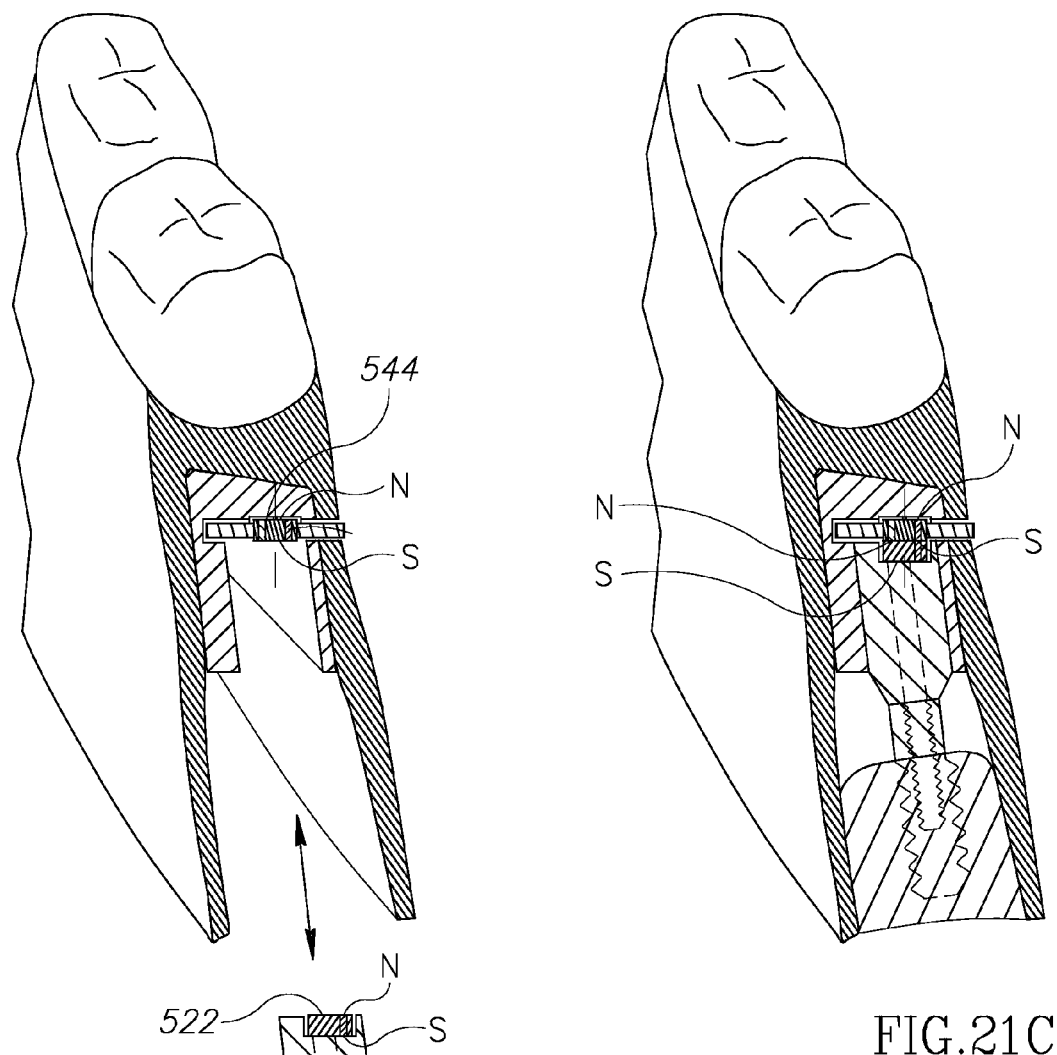
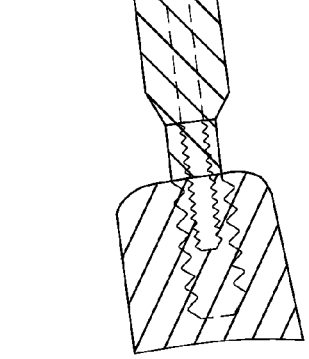
FIG.21D
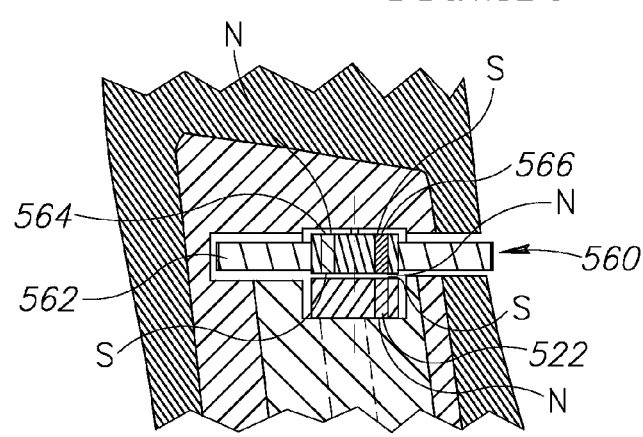
FIG.21C
FIG.22B

DENTURE STABILIZATION SYSTEM AND METHOD

FIELD OF THE INVENTION

The present disclosed subject matter is generally in the field of dental dentures. More particularly the disclosure relates to a system and method for stabilized mounting of a dental denture, yet at a readily removable fashion.

BACKGROUND OF THE INVENTION

Partial or complete loss of an individual's natural teeth, either or both at the upper and lower jaw, due to age, accident, diseases or other reasons has some serious effects on an individual, both functionally and socially. Lack of teeth poses several serious functional problems such as not being able to chew, speech difficulties, etc. Even more so, a smile with a full set of white teeth is considered something to be desired, i.e. esthetics play an important role in life.

While a denture can be accurately fitted to the alveolar ridge of an individual, it is difficult to retain a denture in position. That is, during normal chewing or talking, the denture has a tendency to ride up out of position on the alveolar ridge, causing speech difficulties, chewing difficulties, and general unsatisfactory use of a denture.

A denture is a removable dental prosthesis which has artificial teeth embedded in a denture base resembling the gum or gingiva. The denture base provides the support for the prosthesis by resting on the gingiva or over a support bar secured to the respective jaw bone by a plurality of dental implants. The underside of the denture base has a depression receptacle that receives at least a portion of the gingiva or support bar, so as to provide a snug, reversible fit of the denture.

In recent years practice has developed of permanently implanting dental implants (at times referred to as dental fixtures or posts) in the bone structure of the mouth. These permanent dental implants are made of hard material acceptable by the body's biological processes (e.g. titanium) and which are locked into position by bone growth. By utilization of the permanently installed implants in the mouth of the individual, the possibility then exists for more readily securing a denture in place either fixedly or removably.

WO06103648 discloses a removable denture system comprising a support beam fixedly attached to the individual's alveolar ridge above the mucous membrane by a plurality of dental implants, and a denture generally conforming with the dental parameters of the individual and integrated with a super-structure. The super-structure comprises at least a portion shaped in confirmation with the support beam, and a denture locking arrangement for removably though fixedly articulating the denture to the support beam preventing unintentional disengagement of the denture.

U.S. Pat. No. 5,013,243 discloses a denture attachment including a magnet body, to be embedded in a denture base, comprises a pair of soft magnetic alloy end plates, a non-magnetic alloy spacer disposed between the end plates, and a cap covering the magnet body, the end plates and the spacer except on the side of a coping. The attachment causes a magnetic attractive force of the magnet body to act on the coping of a soft magnetic alloy embedded in a pulp cavity of a tooth deprived of the crown, whereby the denture base is stabilized on gingiva. The magnet body is disposed with its N and S poles facing the end plates, respectively.

SUMMARY OF THE INVENTION

According to the present disclosed subject matter there is disclosed a removable denture system comprising a support beam fixedly attached to the individual's alveolar ridge above the mucous membrane by a plurality of dental implants, and a personalized denture conforming with the dental parameters of the individual and integrated with a super-structure. The super-structure extends along a major portion of the denture and is shaped in confirmation with the support beam for snugly embracing the support beam. One of the super-structure and the support beam is configured with at least one groove or projection, and the other of the super-structure and the support beam is configured with an oppositely extending corresponding at least one projection or groove for engagement therewith, wherein the at least one projection and groove extend along the Path Of Insertion (POI) of the denture. The removable denture system is further configured with a denture locking arrangement for removably though fixedly articulating the denture to the support beam preventing unintentional disengagement of the denture. The one or more grooves and projections serve for improving rigidity and grip of the super-structure over the support beam and for easing mounting (guiding) of the super-structure over the support beam.

The term path of insertion (POI), (also known as 'path of placement') denotes a specific imaginary line along which the denture is placed onto or removed from the support beam, said line intersecting the occlusal plane of the individual's mouth.

The term occlusal plane denotes the imaginary surface on which upper and lower teeth (or dentures) meet.

According to a first aspect of the disclosed subject matter there is provided a removable denture system comprising a personalized support beam fixedly attached to an individual's alveolar ridge above the mucous membrane by a plurality of dental implants; a personalized denture conforming with dental parameters of the individual and having fixedly integrated within a bottom surface thereof a super-structure having a cross-section conforming with that of the support beam; and a denture locking arrangement for securely locking and unlocking the denture to the support beam, at substantial zero tolerance therebetween, and wherein one of the support beam and the super-structure is configured with one or more positioning grooves extending parallel to a path of insert (POI) of the denture, and the other of the support beam and the super-structure is configured with corresponding one or more laterally projecting positioning projections, each extending in register with a corresponding positioning groove and configured for snug sliding there within.

A denture according to the present disclosed subject matter may be configured with any one or more of the following designs and features:

- the one or more positioning grooves and/or the one or more positioning projections are configured with a cross-section tapering in direction of the path of insertion, and/or in a labial or lingual direction (i.e. the positioning projections converges in direction of the POI, whilst the positioning grooves diverge in that sense;
- easy and correct positioning of the super-structure over the support beam is facilitated by providing a directive funnel-like arrangement by either a widening of one or more of the positioning grooves at their top ends and/or narrowing of the positioning projections at their bottom end;
- the one or more positioning grooves and the corresponding one or more positioning projections are configured on either or both a labial face and a lingual face of the super-structure and the support beam, respectively;

at least the one or more positioning grooves extend the entire height of the respective support beam or super-structure;

where the positioning projections are configured on support beam, the super-structure follows the shape of the support beam, maintaining substantially the same thickness; with corresponding decrease of thickness of the personalized denture;

each of the personalized denture, super-structure and support beam may be made of any rigid, metallic or non-metallic material such as, for example, metals-gold, titanium, chrome-cobalt, zirconium, zirconium-oxide, porcelain, ceramics, plastic/acrylic/polymeric materials, composite materials, and combinations thereof.

When the material of which the personalized denture is a structural material, there is need to apply thereto a finishing layer mimicking the shape, size, color and texture of the natural teeth the one or more positioning grooves and the one or more positioning projections are configured for sliding engagement, e.g. in the form of dove-tail management;

the one or more positioning grooves and the one or more positioning projections may be configured at a variety of shapes having different cross-sections, e.g. rounded, polygonal etc.;

the one or more positioning projections may extend the entire height of the corresponding positioning grooves, or a restricted portion thereof, and may also be configured in the shape of protuberances, pins and the like;

the one or more positioning grooves and the one or more positioning projections are configured at a staggered arrangement over the labial face and an lingual face;

the one or more positioning grooves and the one or more positioning projections are configured in registered arrangement over the labial face and an lingual face;

the positioning projections may be configured such that the bottom base is wider than the top base, both in a plane extending along a posterior-anterior direction, and at a plane substantially parallel to the support beam;

one of the lower surface of the super-structure and an upper surface of the support beam is configured with recesses and the other of the lower surface of the super-structure and an upper surface of the support beam is configured with corresponding protuberances in register with said recesses;

the recesses and the corresponding protuberances may extend at a radial or other aspect (orientation)

a top surface of the support beam, and respectively a lower surface of the super-structure may be substantially flat or may be fitted with a ridge. The top surface of the support beam, and respectively a lower surface of the super-structure may be uniform or alter along the length thereof;

the side walls (lingual and labial walls) of the support beam, and respectively those of the super-structure may be substantially parallel to one another or inclined with respect to one another (and with respect to the path of insertion), said inclination being in the range of between about 0° to 30°.

It is however important that the wall surfaces (lingual, labial and bottom) of the super-structure follow and correspond with the shape of the respective walls (lingual, labial and top) of the support beam and all said walls and surface are at substantially full contact surface with each other in a tight and snug fit, cancelling tolerances to thereby ensure motionless fitting of the denture over the support beam and however facilitating for its easy mounting and removal, per demand only.

The provision of laterally projecting positioning projections over the support beam plays a further role in reinforcing the support beam and in increasing the resistance of the support beam to bending moments, shear moments and torsion moments acting on the support beam. In particular, provision of such positioning projections adjacent location of bores formed in the support beam for securing to the dental implants significantly increases resistance of the support beam to bending moments, shear moments and torsion moments acting on the support beam, rendering it competent for bearing significant forces applied during chewing, biting and tearing actions performed by the individual wearing a denture. That is even more so when considering proximal locations of dental implant bores.

According to another aspect of the present disclosed subject matter there is disclosed a locking mechanism for a removable denture, configured to facilitate rigid securing of the denture to the support beam in a substantially tolerance-free fashion, such that when locked it will not spontaneously detach from the support beam and however enabling easy and readily unlocking and removal of the denture.

A locking arrangement according to the present disclosure may comprise one or more locking mechanisms.

The one or more locking mechanisms may be configured at the posterior end of the denture system and/or at middle portions thereof.

The one or more locking mechanisms may be fitted at a lingual and/or labial face of the denture, or at a top face thereof.

According to a first design of the locking mechanism, there is provided at least one first magnet fixed within the support beam and oriented with a one pole facing upwards; a disc-like manipulator received within the denture and rotatable about an axis substantially parallel to an axis of said first magnet; said manipulator projecting partially from at least a lingual or labial face of the denture and fixedly bearing at least one second magnet oriented with an opposite pole facing the support beam; said disc-like manipulator being displaceable between a locked position wherein said least one second magnet extends substantially coaxial with said at least one first magnet, giving rise to attraction force therebetween and wherein the denture is attracted to the support beam, and an unlocked position, upon rotating the disc-like manipulator, whereby the attraction force significantly diminishes so as to allow removal of the denture.

One of the first magnet and second magnet may be a piece of ferrous metal configured for attraction to the magnetic member provided at either the support beam or the denture.

According to one example, there is provided a further second magnet (a rejecting magnet), however with its poles reversely oriented with respect to said second magnet (i.e. oriented like the first magnet), whereby positioning the disc-like manipulator with the further second magnet extending over the first magnet results in rejecting force therebetween, facilitating in extracting/removal of the denture;

According to a particular design the disc-like manipulator traverses the super-structure.

According to a particular design, the locking mechanism is configured at the posterior end of the denture.

Where two first magnets are provided, they extend along an arch line of the denture, wherein the disc-like manipulator is displaced at 90° between its respective positions. Where only one first magnet is provided, the disc-like manipulator is displaced at between 90°-270° into the unlocked position.

According to a different configuration, the locking mechanism comprises one or two locking recesses configured on the support beam and the denture is configured with a disc-like manipulator received within the denture and rotatable about a substantially vertically extending axis and projecting partially from at least a lingual or labial face of the denture, said disc-like manipulator configured with one or two locking members configured for locking arresting said locking recesses; wherein said disc-like manipulator is displaceable between a locked position wherein said one or two locking members are arrested within the recesses, and an unlocked position upon rotating the disc-like manipulator, whereby the locking members disengage from the respective recesses.

According to one particular design the locking members tangentially extend from the disc-like manipulator.

The locking recesses are configured within or over a top surface of the support beam. The design is such that the locking mechanism, according to any of the configurations disclosed herein, in itself does not bear loads, i.e. when the denture is mounted over the support beam, during chewing, forces react substantially between the super-structure and the support beam, and substantially no forces are born by the locking system.

Furthermore, a locking mechanism may be further configured with an arrangement designed to assist in unlocking thereof, from a labial direction.

BRIEF DESCRIPTION OF THE DRAWINGS

In order to understand the disclosed subject matter and to see how it may be carried out in practice, examples will now be described, by way of non-limiting examples only, with reference to the accompanying drawings, in which:

FIGS. 7A and 7B are exploded perspective views of a denture system in accordance with a different example of the present disclosed subject matter, the denture illustrated at its upright position;

FIGS. 11A and 11B are a labial perspective view and a top view, respectively, of a support beam in accordance with another example of the present disclosed subject matter;

FIGS. 12A and 12B are a perspective labial bottom view and a bottom view, respectively, of a denture configured for use in conjunction with the support beam of FIGS. 11A and 11B;

FIGS. 13A and 13B are a labial perspective view and a top view, respectively, of a support beam in accordance with a different example of the present disclosed subject matter;

FIGS. 14A and 14B are a perspective labial bottom view and a bottom view, respectively, of a denture used in conjunction with the support beam of FIGS. 13A and 13B;

FIG. 21C is a longitudinal section illustrating the denture system fitted with a locking mechanism of the disclosed example at the mounted, arrested position;

FIG. 21D illustrates a denture system wherein the denture is removed from the support beam;

FIG. 22B is a section taken along line D-D in FIG. 22A;

DETAILED DESCRIPTION OF EMBODIMENTS

Figures 1A, 1B, 1C:
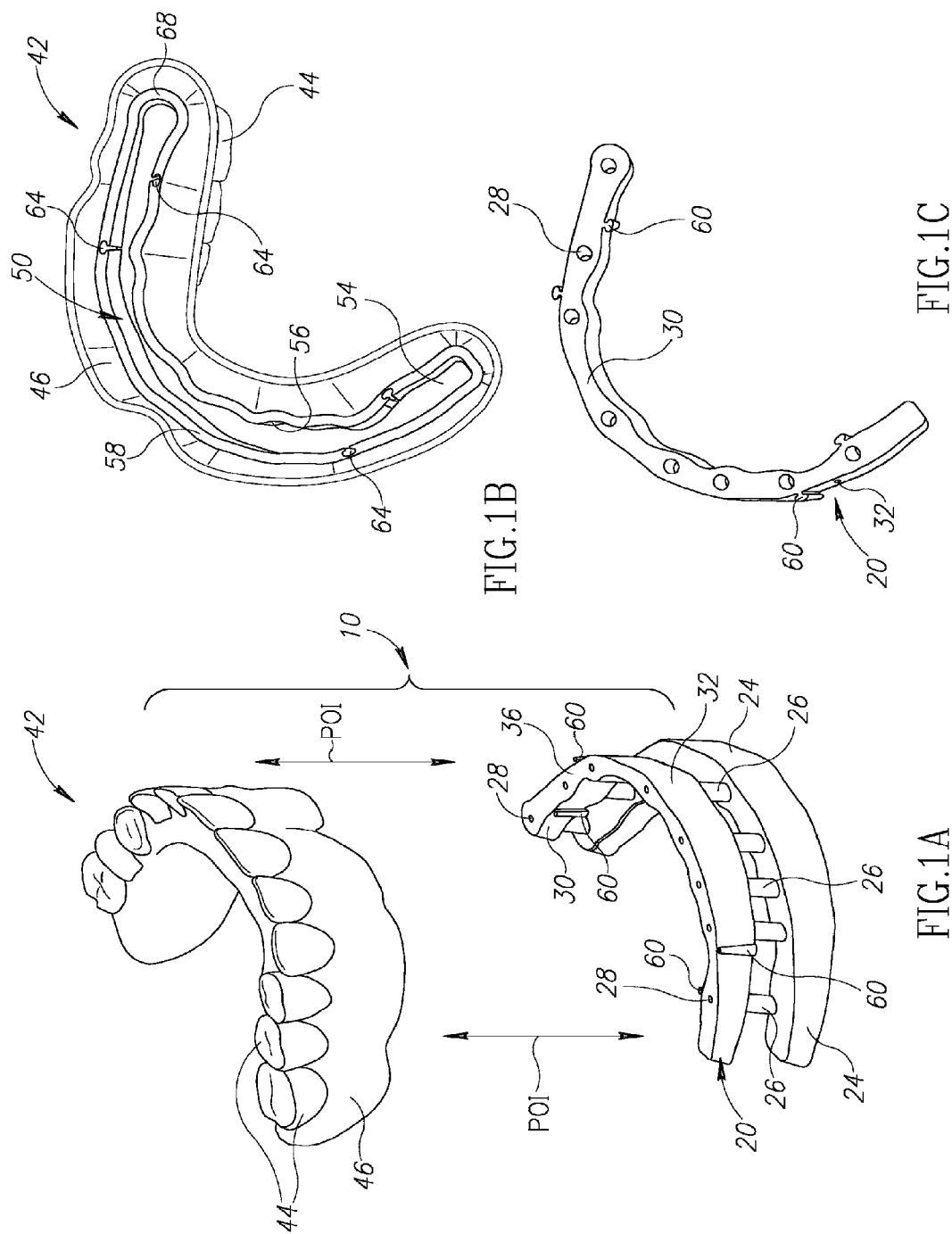
FIGS. 1A to 1C illustrate an exploded isometric view of a denture system in accordance with an example of the present disclosed subject matter, showing mounting and removal of the denture and a bottom view of the denture and a support bar.
Figure 2:
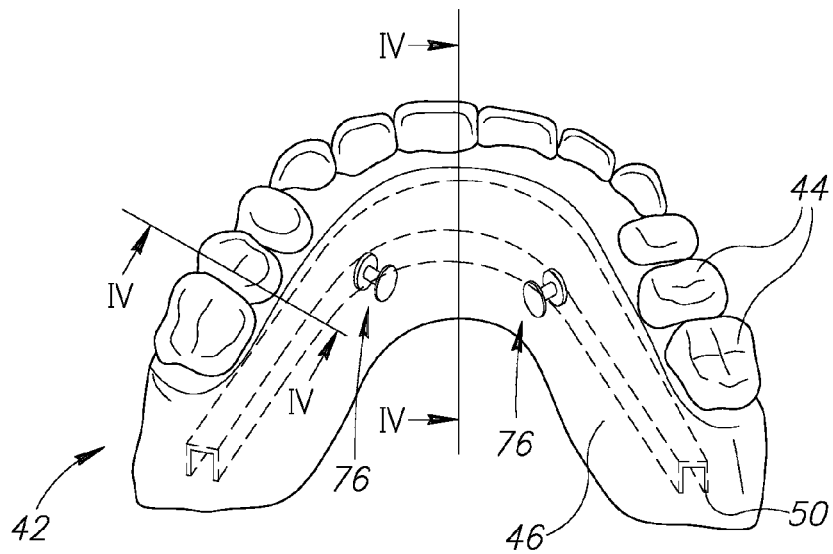
FIG. 2 is a lingual view of the denture of FIGS. 1A and 1B.
Figure 3:
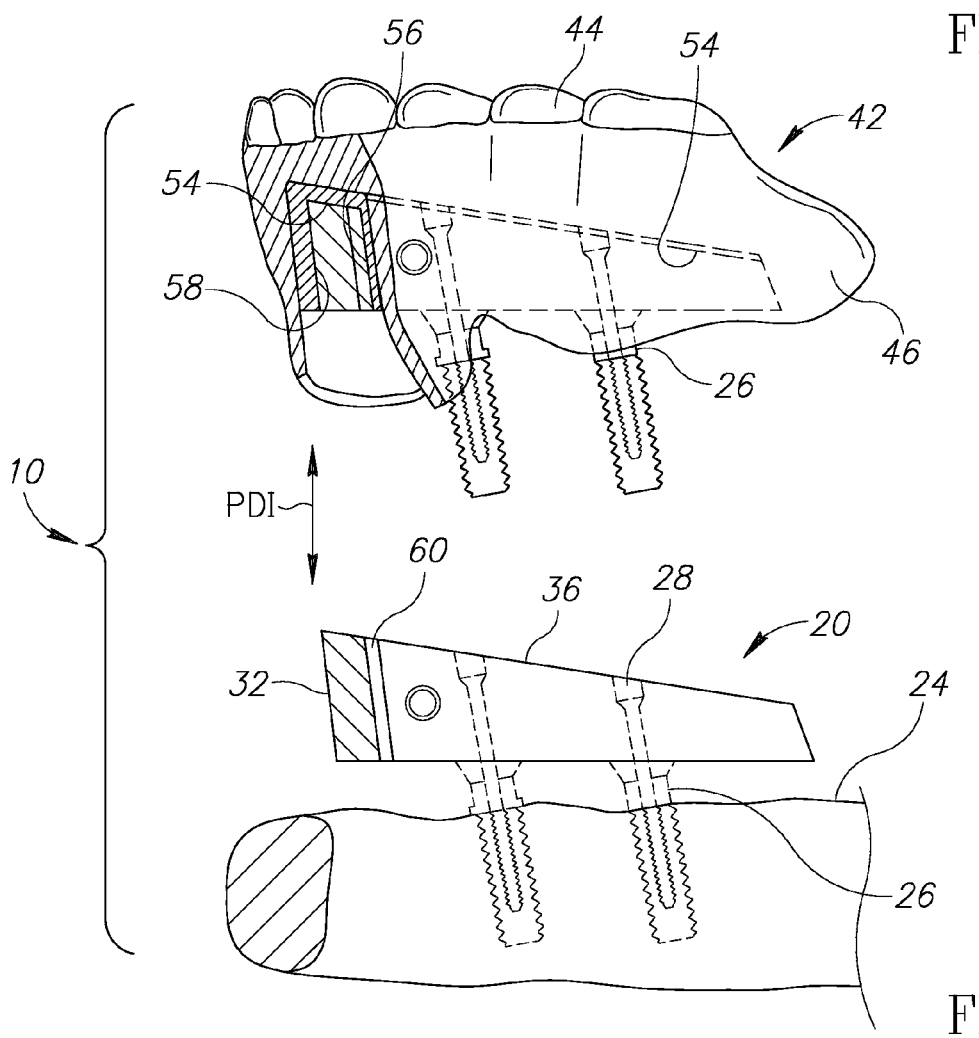
FIG. 3 is an exploded posterior view, partially sectioned, of the denture system in accordance with the present disclosed subject matter.
Figure 4:
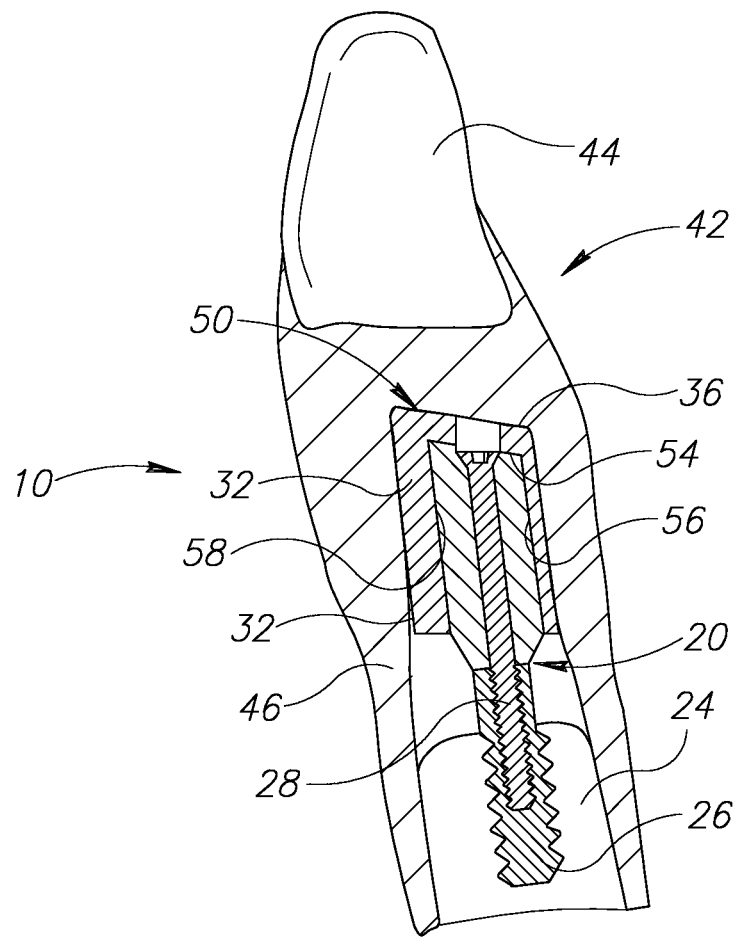
FIG. 4 is a section along line IV-IV in FIG. 2.
Figure 6A:
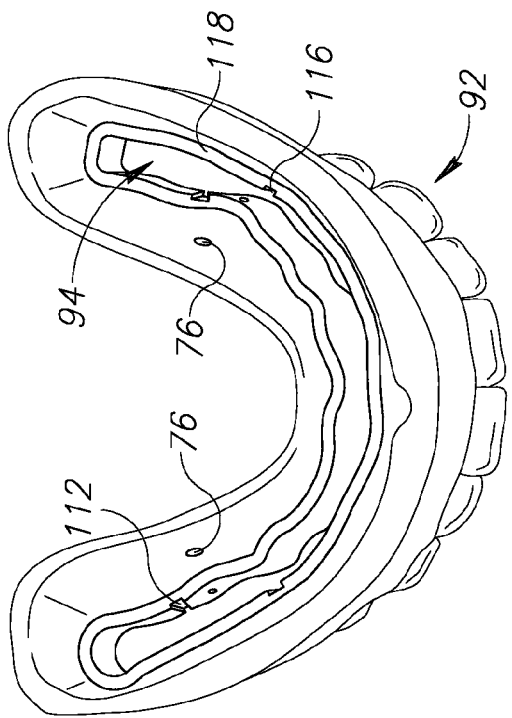
FIGS. 6A and 6B are perspective labial bottom view and bottom view, respectively, of a denture in accordance with the present disclosed subject matter; configured for use in conjunction with the support beam of FIGS. 5A and 5B.
Figure 6B:
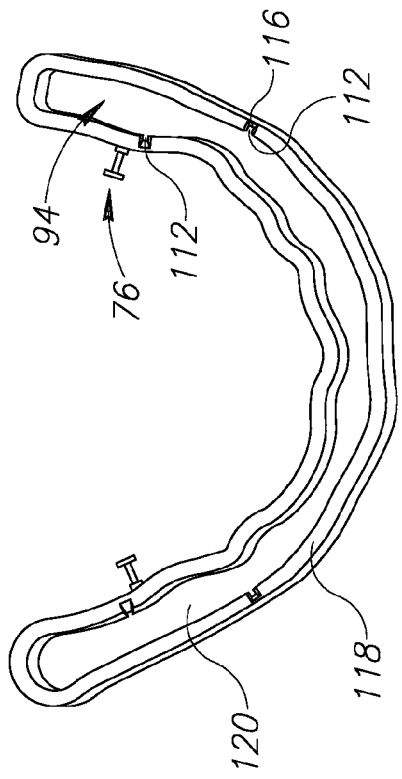

Attention is first directed to FIGS. 1A-1C to 4 of the drawings illustrating a denture system generally designated 10, in accordance with the present disclosed subject matter. The denture system 10 comprises a support beam 20 fixedly secured to a jaw bone 24 (i.e. to the individual's alveolar ridge above the mucous membrane) of an individual, by a plurality of dental implants 26 received within the jaw bone 24 and wherein the support beam 20 is secured to said dental implants 26 by appropriate screws 28.

The support beam 20 follows the general arched shape of the jaw 24 and is configured with a lingual (inside) face 30, a labial (external) face 32 and a top surface 36.

It is apparent from the drawings that the top surface 36 of the support beam 20 is substantially flat and smooth over its entire length.

The denture 42 is configured for detachably mounting over the support beam 20 as will be discussed hereinafter and is personalized so as to conform with dental parameters of the individual namely comprises a plurality of teeth 44 resembling the natural teeth of the individual as far as shape, size and color, and a gum-mimicking portion 46 configured to extend below the support beam when mounted thereon and to cover at least a portion of the mucous membrane (the natural gum portion of the individual). Fixedly integrated within a bottom surface of the personalized denture 42 there is a super-structure 50 having a cross-section conforming with that of the support beam 20 and adapted for snuggly mounting thereover at substantially zero tolerance for which purpose it is provided with an upper wall 54 being substantially flat and smooth configured for flush positioning over the top surface 36 of the support beam 20 and corresponding lingual surface 56 and labial surface 58 for smooth, flush engagement with the corresponding lingual surface 30 and labial surface 32 of the support beam 20.

Manufacture of the support beam 20 and the personalized denture 42 is disclosed for example in U.S. Pat. No. 7,806,691.

It is appreciated that the personalized denture 42 is configured for applying and removal from the support beam 20 along a path of insertion (POI) namely the imaginary line along which the personalized denture 42 is placed onto, or removed from the support beam 20, intersecting the occlusial plane of the individual's mouth.

As can further be seen, in particular in FIGS. 1A and 1B, the support beam 20 is configured with a plurality of laterally projecting positioning projections 60 (four in the present case, two at each of the lingual surface 30 and labial surface 32) said positioning projections 60 extending parallel to the path of insertion and parallel to one another, whilst the super-structure 50 is configured with a corresponding number of positioning grooves 64 extending in register with the positioning projections 60 namely configured for snuggly sliding there over at substantially zero tolerance.

It is noted, in the particular example, that the positioning projections 60 extend the entire height of the support beam 20 and are configured with a rounded shape such as to minimize irritation upon removal of the personalized denture 42. On the other hand, the positioning grooves 64 extend from the lowermost surface 68 of the super-structure up to the top surface 54 and as mentioned hereinabove, are configured for snug sliding over the positioning projections 60.

Figure 19B:
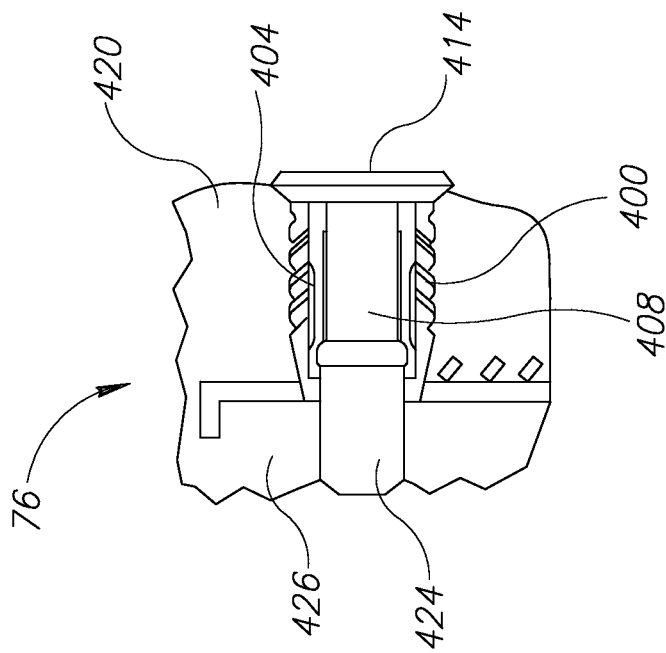
FIGS. 19A and 19B illustrate a sectioned portion along line V-V in FIG. 2, illustrating a retractable pin-type locking mechanism at its respective unlocked and locked position.
Figure 19A:
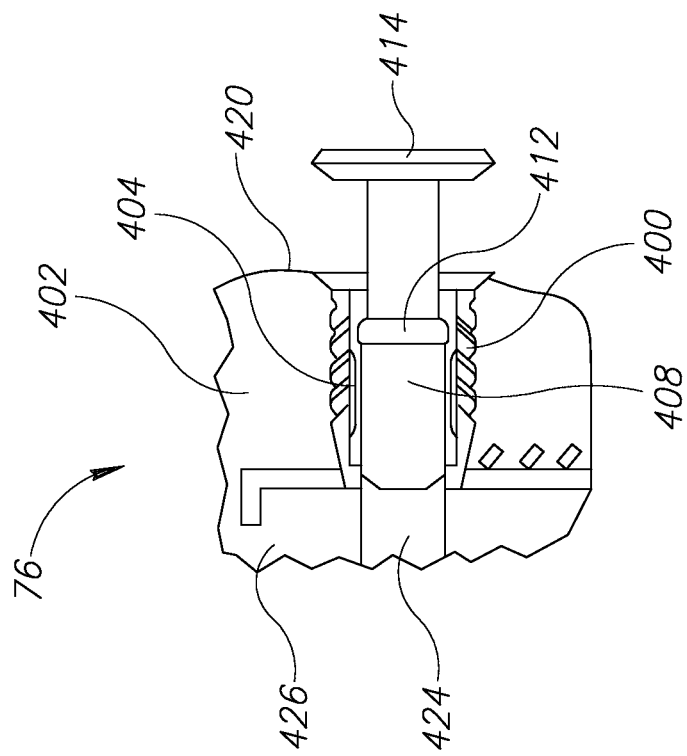
Figure 20C:
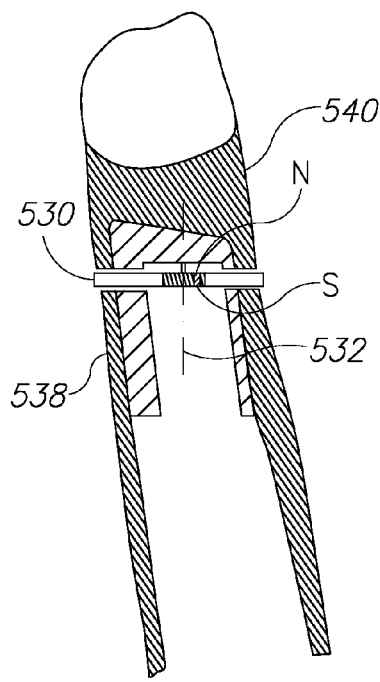
FIG. 20C is a longitudinal section along line C-C in FIG. 20A.
Figure 20B:
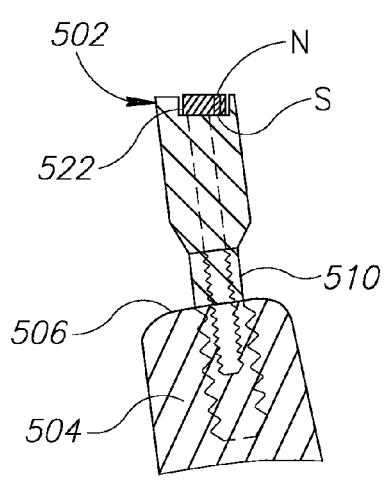
FIG. 20B is a longitudinal section along line B-B in FIG. 20A.
Figure 20A:
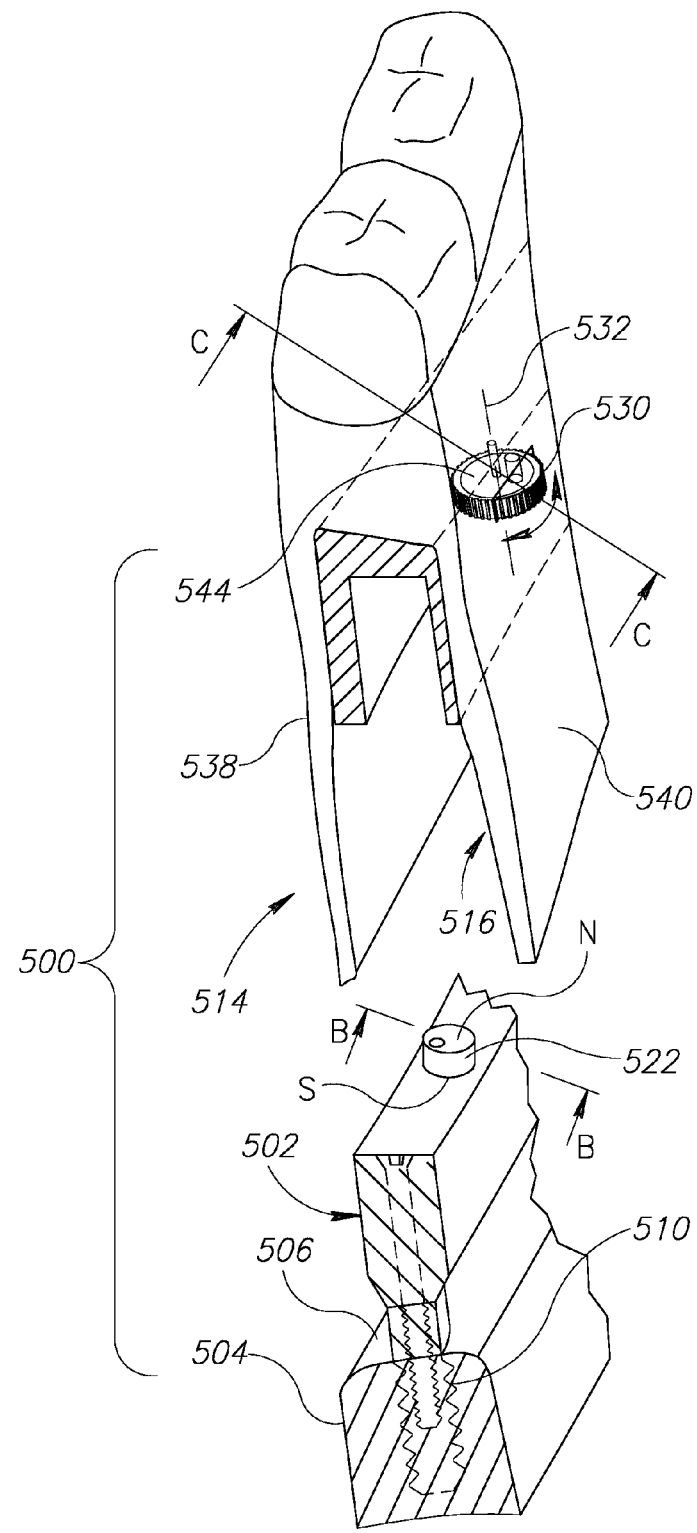
FIG. 20A is an exploded perspective sectioned view of a locking mechanism for use in conjunction with a denture system of the disclosed subject matter.

The denture system 10 is further configured with a locking mechanism 76 which in the present example is a pin-type locking arrangement disclosed in further detail in FIGS. 19A and 19B.

Further attention is now directed to FIGS. 5A-5B and 6A-6B of the drawings wherein the general features of the support beam generally designated 90 and the personalized denture generally designated 92 with the integrated super-structure generally designated 94 substantially follow the features as discussed hereinabove in connection with FIGS. 1A-1C to 4.

Figure 5A:
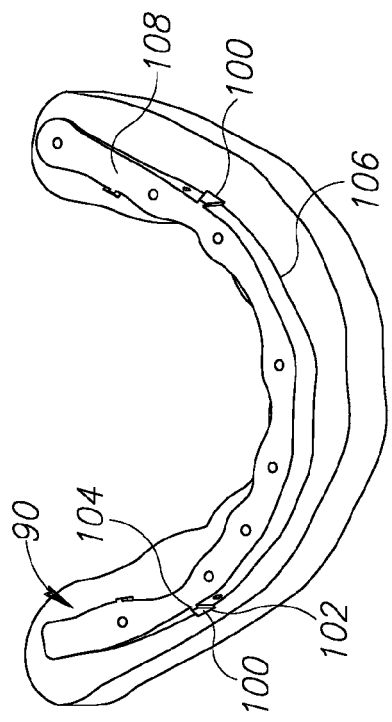
FIGS. 5A and 5B are a labial perspective view and top view, respectively, of a support beam in accordance with an example of the present disclosed subject matter.
Figure 5B:
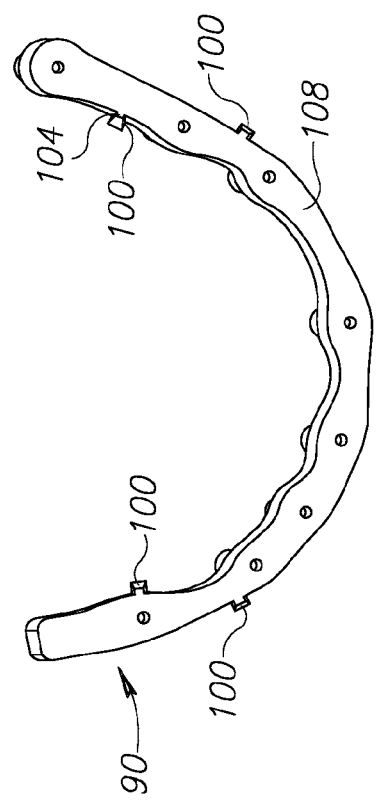
Figure 9A:
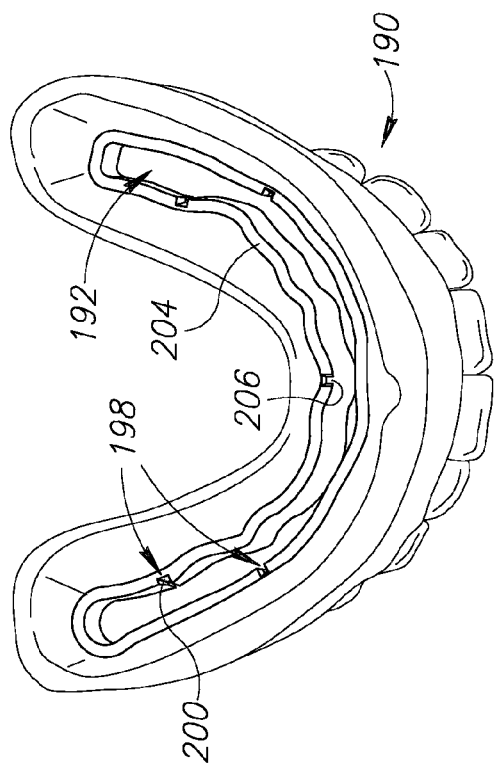
FIGS. 9A and 9B are a labial perspective bottom view and a bottom view, respectively, of a denture in accordance with the present disclosed subject matter, configured for use in conjunction with the support beam of FIGS. 8A and 8B.
Figure 9B:
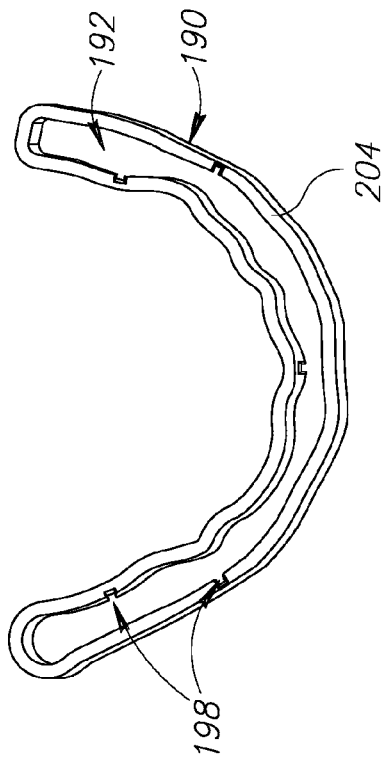
Figure 8A:
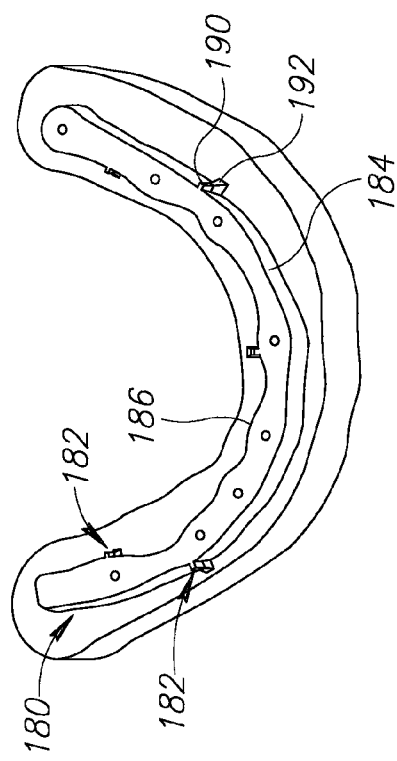
FIGS. 8A and 8B are a labial perspective view and a top view, respectively, of a support beam in accordance with yet an example of the present disclosed subject matter.
Figure 8B:
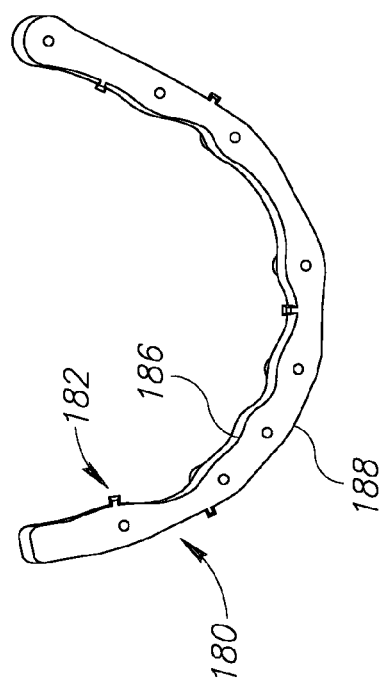

However, in the particular illustrated example of FIGS. 5A and 5B the positioning projections 100 are trapezoidal with a wide bottom base 102 narrowing upwards towards a top narrow base 104 wherein, in the particular example, the bottom base 102 extends down towards a bottom edge 106 of the support beam 90 and the top base 104 extends flush with a top, flat surface 108 thereof. In correspondence therewith, the super-structure 94 is configured with four corresponding positioning grooves 112 each having a cross-section corresponding with that of the positioning projections 100 of the support beam 90 i.e. the positioning grooves 112 have a tapering cross-section with a wide opening 116 extending at a lowermost surface 118 of the super-structure 94 and with a narrow top portion extending at the inner surface 120 of the super-structure 94, configured for flush bearing over the top surface 108 of the support beam 90.

It is appreciated that the trapezoidal configuration of the positioning projections 100 and the corresponding positioning grooves 112 facilitate easy mounting of the personalized denture 92 over the support beam 90 whereby the wide opening 116 of the positioning grooves 112 is placed over the narrow, top base 104 of the positioning projections 100 thus providing a funnel-like arrangement easing placing of the personalized denture over the support beam 90, however not deteriorating the firm support of the personalized denture 92 over the support beam 90 when fully received thereon.

Further notice, the denture system collectively illustrated in FIGS. 5A-5B and 6A-6B is configured with a pin-like locking mechanism 76 of the type disclosed hereinafter with further detail in FIGS. 19A and 19B.

Turning now to FIGS. 7A and 7B there is illustrated a modification of the example illustrated in FIGS. 5A-5B and 6A-6B. According to this example, the support beam generally designated 140 is configured with positioning projections 142 laterally projecting from the lingual surface and labial surface, respectively, and extending parallel to the path of insertion as discussed hereinabove. However, the positioning projections 142 have a trapezoidal cross-section (similar to the disclosure of FIGS. 5A and 5B) namely having a wide bottom base 146 and a narrow top base 148, said top base extending flush with the top surface 150 of the support beam 140, and further when each of the positioning projections 142 is configured as a dove-tail configuration, configured for sliding engagement within the corresponding positioning grooves 156 formed at the super-structure 160 of the personalized denture 162. Accordingly, the positioning grooves 156 have a like configuration so as to snugly slide over the positioning projections 142 namely are configured with a trapezoidal cross-section extending between a bottom, wide opening at 164 and narrowing upwards towards the upper surface 170 of the super-structure 160.

It is appreciated that the dove-type positioning configuration of grooves and projections reduces any possible tolerances between the super-structure and the integrated personalized denture whilst mounted over the support beam, thus eliminating any movement.

It is further appreciated that the provisions of the laterally projecting positioning projections significantly increases resistance of the support beam to bending moments, shear moments and torsion moments acting on the support beam, thus increasing its stability and endurance. On the other hand, it is appreciated that at those locations where the super-structure is provided with positioning grooves, the overall thickness of the walls of the super-structure are not thinner but rather maintain a substantially uniform thickness.

With further attention being made to FIGS. 8A-8B and 9A-9B there is now illustrated yet another example of a denture system in accordance with the present disclosed subject matter resembling, to a wide extent the configuration of FIGS. 5A-5B and 6A-6B, however wherein the support beam 180 is configured with a plurality of positioning projections generally designated 182 wherein in this example two lateral positioning projections extend from the front, labial surface 184 and three positioning projections 182 extend from the inside, lingual surface 186. It is noted that the positioning projections 182 are configured with a substantially straight portion 190 extending parallel to the path of insertion (POI) and having a substantially rectangle cross-section though with chamfered/rounded edges to cause minimal irritation to the individual, and further there is a lower widening portion 192.

Correspondingly, the personalized denture 190 is configured with an integrated super-structure 192 configured with corresponding positioning grooves 198 wherein a bottom opening thereof designated 200, substantially flush with a lowermost surface 204 of the super-structure 192 is substantially wider and narrows upwardly into a rectangular form at 206 with a shape matching that of the corresponding positioning projections 182 and configured for snugly mounting thereon. The widening opening at 200 facilitate easy mounting and positioning of the personalized denture 190 over the support beam 180 wherein upon placing the personalized denture 190 and positioning it over the support beam 180 becomes fixedly positioned and without any tolerances therebetween as discussed hereinabove.

Likewise, the positioning projections may be configured such that the bottom base is wider than the top base, both in a plane extending along a posterior-anterior direction, and at a plane substantially parallel to the support beam (FIGS. 10A-10D).

It should be appreciated, in connection with any of the examples discussed herein the specification, that the number of positioning projections and respective positioning grooves may change as well as their location and their shape and size. Accordingly, one denture system may comprise several different types of positioning projections and corresponding positioning grooves, as long as the general concept of snug fitting resides, with substantially zero tolerance therebetween.

Figure 10B:
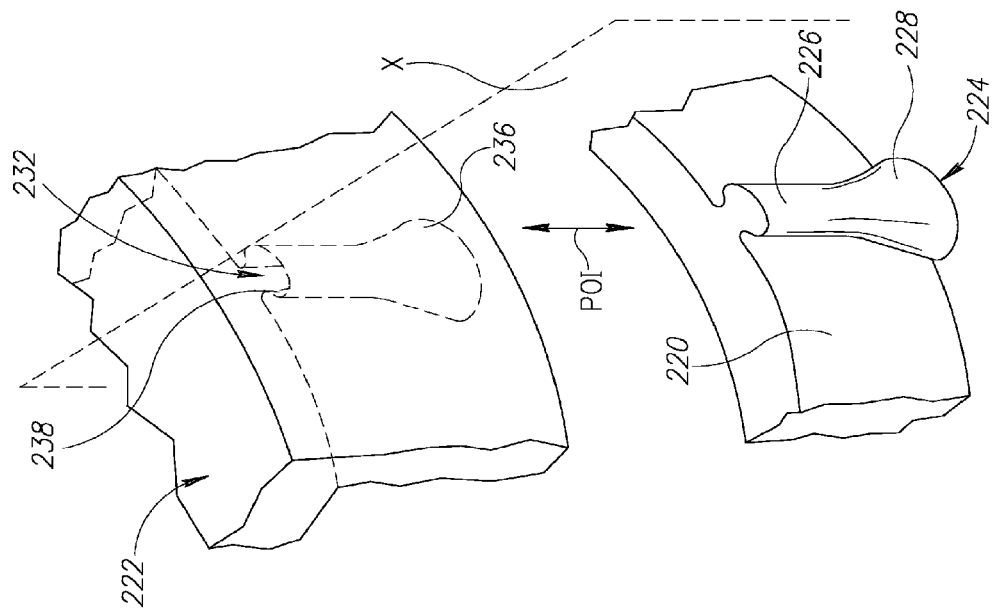
FIGS. 10A and 10B are a schematic illustration, at enlarged scale, of a labial portion of the support beam illustrated in FIG. 8A and a respective portion of the super-structure illustrated in FIG. 9A.
Figure 10A:
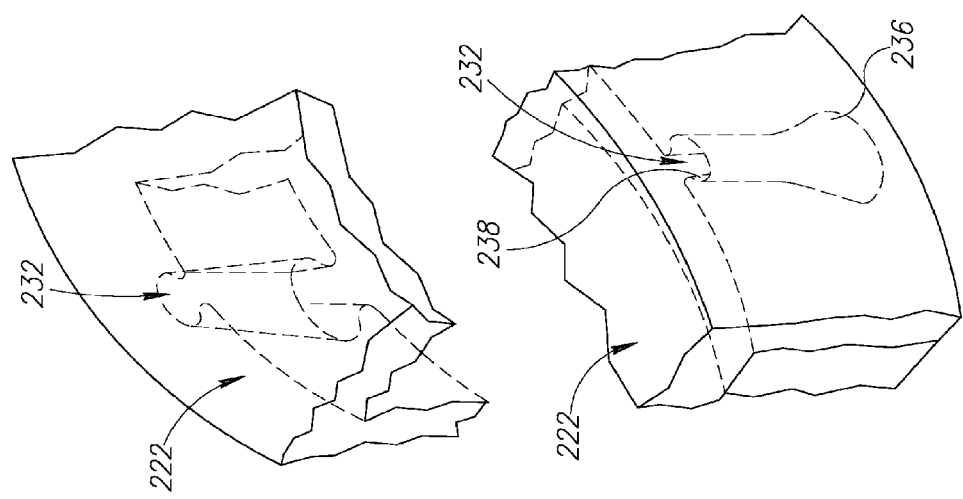

FIGS. 10A and 10B illustrate, at enlarged scale, only a portion of a support beam 220 and a portion of a corresponding super-structure 222 wherein the positioning projection 224 configured on the support beam 220 is a combined configuration having a dove-tail arrangement, with a top portion 226 extending substantially parallel to the POI and a bottom portion 228 tapering in both a lateral and a planar direction (see also FIGS. 10A, 10B and 10D) and wherein the corresponding positioning groove 232 of the super-structure 222 has a widening opening at its bottom edge 236 narrowing upwards and terminating at a top end 238, corresponding in cross-section with the positioning projection 224.

Figure 10D:
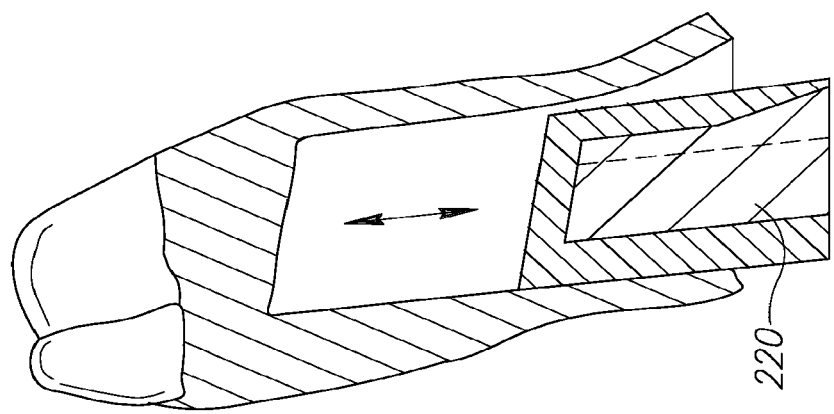
FIGS. 10C and 10D illustrate a longitudinal section through a denture system showing consecutive steps of mounting/removal of the denture.
Figure 10C:
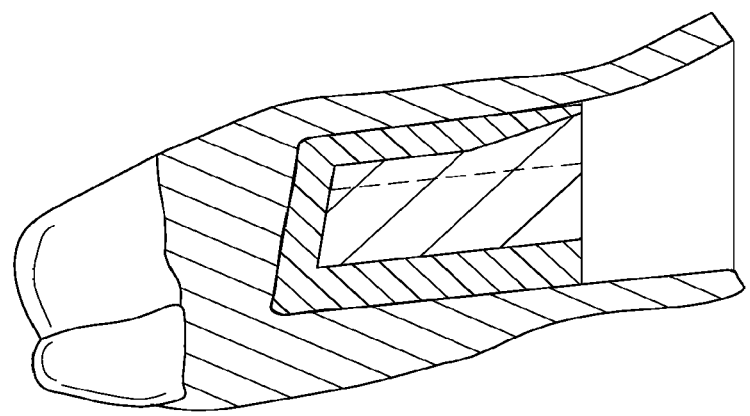
Figure 16A:
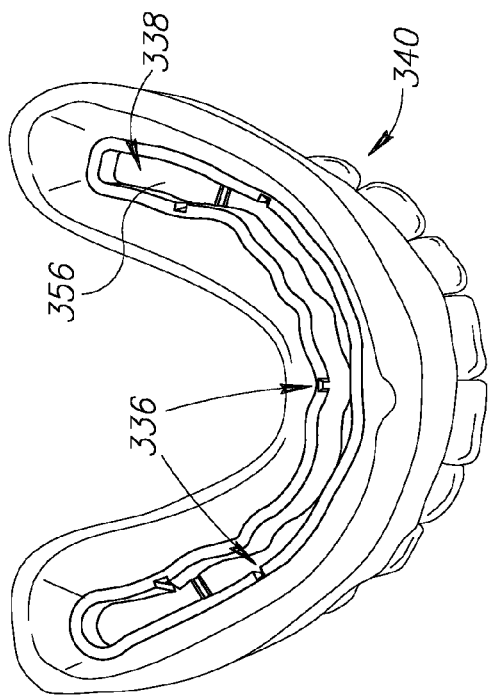
FIGS. 16A and 16B are a perspective labial bottom view and a bottom view, respectively, of a denture used in conjunction with the support beam of FIGS. 15A and 15B.
Figure 16B:
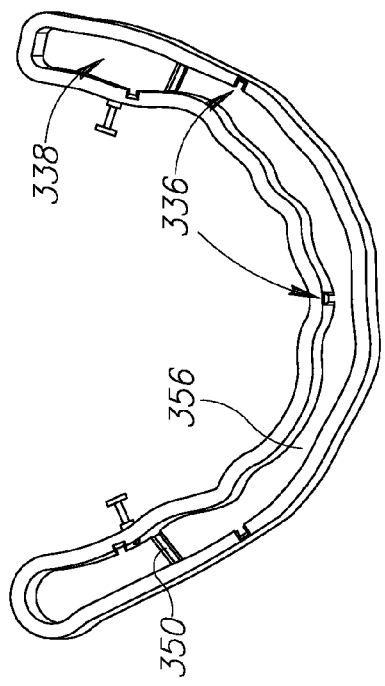
Figure 15A:
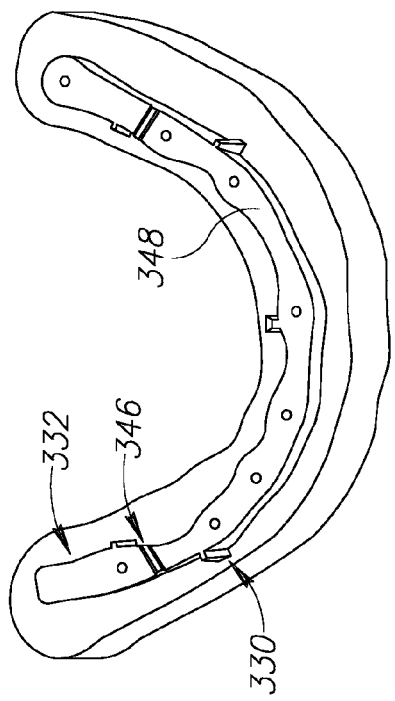
FIGS. 15A and 15B are a labial perspective view and a top view, respectively, of a support beam in accordance with a modified example of the present disclosed subject matter.
Figure 15B:
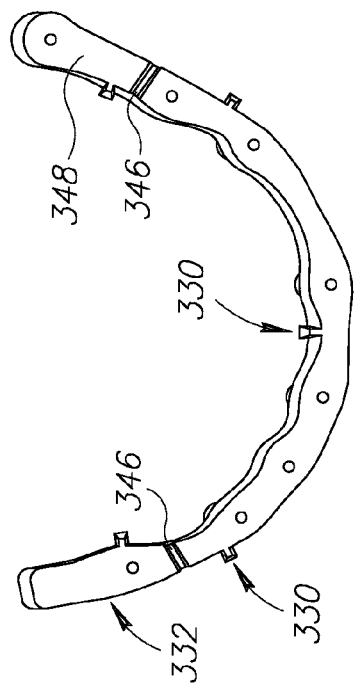
Figure 18B:
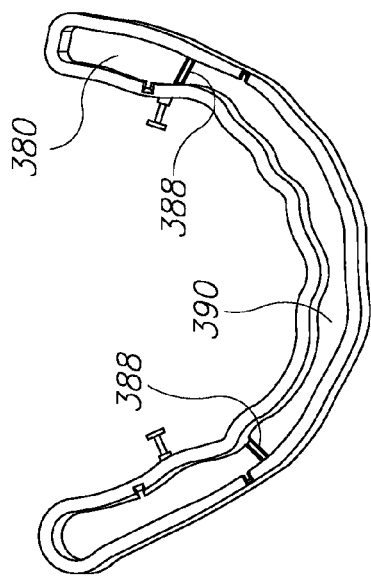
FIGS. 18A and 18B are a perspective labial bottom view and a bottom view, respectively, of a denture configured for use in conjunction with the support beam of FIGS. 17A and 17B.
Figure 18A:
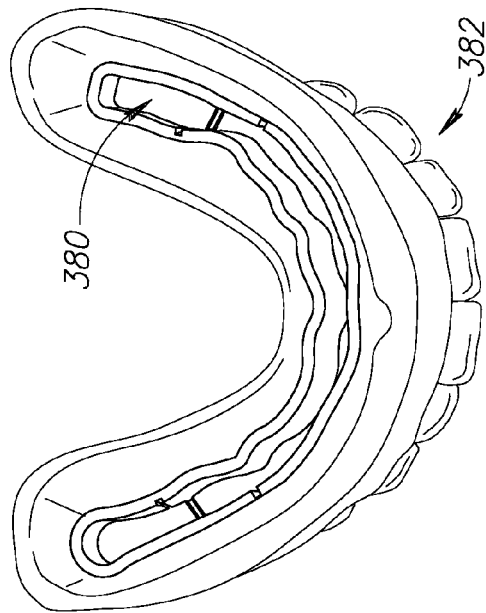
Figure 17B:
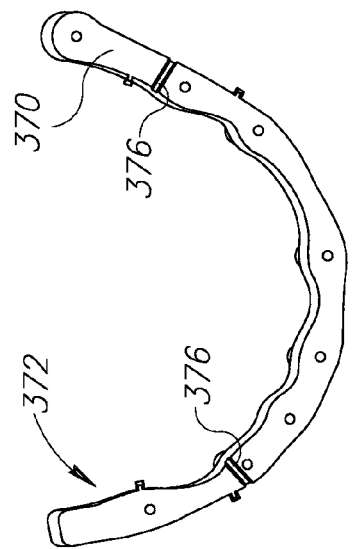
FIGS. 17A and 17B are a labial perspective view and a top view, respectively, of a support beam configured in accordance with a different example of the present disclosed subject matter.
Figure 17A:
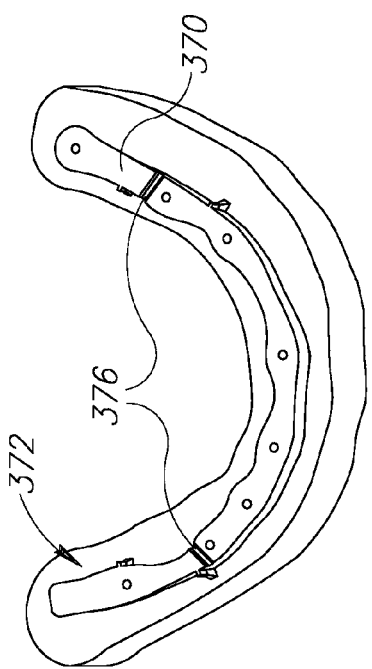

FIGS. 10C and 10D are cross-sections taken along section plane X in FIGS. 10A and 10B illustrating consecutive sets of mounting a personalized denture with the integrated super-structure over a corresponding support-beam, configured with a positioning groove and positioning projection, respectively.

Whilst in the examples illustrated herein so far the positioning projections were configured over the support beam and respectively the positioning grooves were configured at the super-structure, in the following examples of FIGS. 11A-11B to 14A-14B, the positioning projections are configured at the super-structure and respectively the positioning grooves are configured at the support beam.

Turning first to FIGS. 11A-11B and 12A-12B it is noted that the support beam 250 is configured at its labial face 252 with two positioning grooves generally designated 256 and one positioning groove 256 configured on the lingual face 258.

The positioning grooves 256 extend parallel to the path of insertion (POI) of the denture system and, in the particular example, the positioning grooves 256 have a top, widened opening at 260, extending from the top, substantially flat and smooth surface 262 of the support beam 250 and tapering downwards towards a substantially rectangle section 266, in a funnel like configuration.

As noted in FIGS. 12A and 12B, the personalized denture 270 is configured with a integrated super-structure 272 which in turn is configured with three positioning projections 276 configured for snugly and tolerance-free receiving within the corresponding positioning grooves 256 configured on the support beam 250. Thus, each of the positioning projections 276 is configured with a substantially rectangular, lower portion 280 extending from a bottom surface 282 of the super-structure 272, said positioning projections 276 widening at their top portion 286 in a fashion corresponding with the shape of the respective positioning grooves of the support beam 250.

Similar to the previous example, in this case too, the denture system is configured with a locking mechanism which in the present example is a pin-type lock mechanism 76, of the type disclosed hereinafter with particular reference to FIGS. 19A and 19B.

FIGS. 13A-13B and 14A-14B illustrate a modification of the example illustrated in connection with FIGS. 11A-11B and 12A-12B wherein the positioning grooves 290 are configured on the support-beam 292 and respectively, the super-structure 296 of the personalized denture 298 is configured with corresponding positioning projections 300 projecting laterally inwards, namely into the confined space of the super-structure, wherein the positioning grooves 290 and the respective positioning projections 300.

Have a tapering cross-section namely wherein the positioning grooves 290 have a wide top opening 304 extending flush with a top surface 306 of the support beam 292 and terminating at a bottom, narrow base 308 thereof. Respectively, the positioning projections 300 of the super-structure 296 extend from a narrow, bottom base 310 extending flush from a bottom edge 312 of the super-structure 296 and widening upwards towards the top surface 316 of the super-structure 296.

In this example too, the configuration is such that mounting of the personalized denture 298 is facilitated and is directed by the funnel-type arrangement of the positioning grooves, however, upon positioning of the personalized denture to its final location over the support beam it becomes rigidly supported and with substantially zero tolerance i.e. with substantially no motion between the personalized denture and bearing support-beam.

Turning now to FIGS. 15A-15B to 18A-18B there are illustrated different examples of denture systems in accordance with the present disclosed subject matter. FIGS. 15A-15B and 16A-16B resemble in a way the denture system disclosed in connection with FIGS. 5A-5B and 6A-6B respectively, at least as far as the provision and shape of the positioning projections 330 formed on the support beam 332 and the respective laterally projecting positioning grooves 336 configured on the super-structure 338 of the personalized denture 340. However, in addition to said positioning grooves 336 and corresponding positioning projections 330, the denture system of FIGS. 15A-15B and 16A-16B further comprises a set (two in the present example) of upwardly projecting positioning projections 346 extending from the top smooth surface 348 of the support beam 332 with corresponding depressions 350 formed on the top surface 356 of the super-structure 338, in correspondence with said positioning projections 346, thereby increasing the true-position between the respective support beam 332 and the super-structure 338 with the integrated personalized denture 340.

The example of FIGS. 17A-17B and 18A-18B illustrates an arrangement resembling that of FIGS. 15A-15B and 16A-16B however with the laterally positioning projections and corresponding positioning grooves resembling that of FIGS. 8A-8B and 9A-9B, and further when configured on the top, substantially flat surface 370 of the support beam 372 there are configured two positioning grooves 376 whilst the super-structure 380 of the personalized denture 382 is configured with corresponding positioning projections 388 extending from the top, substantially flat surface 390 of the super-structure 380, configured for snugly fitting and receiving within the respective positioning grooves 376 formed on the support-beam 372. It is noted that the respective positioning grooves and positioning projections illustrated in connection with FIGS. 15A-15B and 16A-16B, and 17A-17B and 18A-18B, respectively, extend such that their respective side walls are either parallel to the path of insertion (POI) or constitute an acute angle therewith, and further however wherein the depth of the positioning groove and the corresponding height of the respective positioning projection is such as to ensure surface mating (surface to surface contact) thereof.

As mentioned hereinabove, the denture system disclosed hereinbefore are fitted with a locking mechanism. According to one example, the locking mechanism is a pin-type lock 76, discussed with further detail in FIG. 19A (open, unlocked position) and FIG. 19B (closed, locked position).

The lock 76 comprises a housing 400 rigidly embedded within the personalized denture 402, wherein said housing comprises a sleeve 404 made of or corresponding an elastomeric or ceramic material and furthermore, the lock comprises a locking pin 408 formed with an annular displacement limiting ring 412 configured for snapping arrestment by the sleeve 404, said pin being displaceable between a locked position (FIG. 19B) and an unlocked position (FIG. 19A). The locking pin 408 is fitted with a substantially flat head portion 414 which at the locked position extends in close proximity with the lingual surface 420 of the personalized denture, thus causing minimal irritation to the individual, however facilitating retraction thereof e.g. by the individual's fingernail (for that purpose a small interstice is typically configured between the inner surface of the head 414 and the lingual surface 420) the arrangement is such that the locking pin 408 is fitted for snugly fitting within corresponding bores 424 configured in the respective support-beam 426, however, in a fashion wherein substantially no load is borne by the pin while at the locked position.

In some cases, the personalized denture is fitted with a throughgoing bore also at its labial face, with a corresponding throughgoing locking bore formed in the support beam, wherein in case of difficulty in extracting of the locking pin 414 a sharp article may be inserted through the opening (e.g. a paper staple and the like) to facilitate in pushing the locking pin 414 in the lingual direction into its extracted position (FIG. 19A). However, such an opening on the labial surface of the personalized denture is miniature and hardly visible to the eye.

Turning now to FIGS. 20A-20C and 21A-21D there is illustrated a locking mechanism in accordance with a different configuration of the present disclosed subject matter.

The locking mechanism, generally designated 500 comprises a support beam 502 of the type fixedly attached to an individual's alveolar ridge 504 above the mucous membrane 506 by a plurality of dental implants 510.

The denture system 500 further comprises a personalized denture 514 conforming with dental parameters of the individual and having fixedly integrated within a bottom surface thereof a super-structure generally designated 516 having a cross-section conforming with that of the support beam 502 and configured for snugly and tolerance-free engagement over the support-beam 502. The locking mechanism comprises at least one first magnet 522 fixedly received within the support beam 502 and oriented such that its North pole faces upwards and its South pole faces downwards. A disk-like manipulator 530 is received within the personalized denture 514 and is rotatably secured about an axis of rotation 532 substantially parallel to an axis said first magnet 522. The manipulator 530 laterally projects, partially from at least one or both of the lingual or labial face 538 and 540, respectively and is fixedly fitted with at least one second magnet 544 oriented in an opposite sense and the first magnet 522, namely with its south (S) pole facing downwards and its north (N) pole facing upwards.

The disk-like manipulator 530 is displaceable between a locked position (FIG. 21A) wherein the second magnet 544 extends substantially coaxial and above the first magnet 522, giving rise to a traction force extending therebetween and wherein as a result the personalized denture 514 is attracted to the support beam 520 and will thus not spontaneously detach therefrom. The manipulator 530 is further displaceable into an unlocked position (FIG. 21B), upon rotation of the disk-like manipulator 530 as illustrated by arrowed lines 550, whereby the second magnet 544 displaces from its locked position above the first magnet 522 whereby the attraction force therebetween seizes or substantially diminishes, whereby the personalized denture 514 may be easily removed from the support beam 502.

It is appreciated that the number of locking mechanisms of the aforementioned type fitted in a denture system may vary depending on the space provided in the denture system and accordingly, the attracting force may be controlled by providing magnets with different force and for that purpose small, though powerful magnets (e.g. neo medium magnets) may be used.

Furthermore, it is noted that one of the first magnet 522 and second magnet 544 may be a piece of ferrous metal configured for attraction to the magnetic member provided at either the support beam or the denture.

Figure 22A:
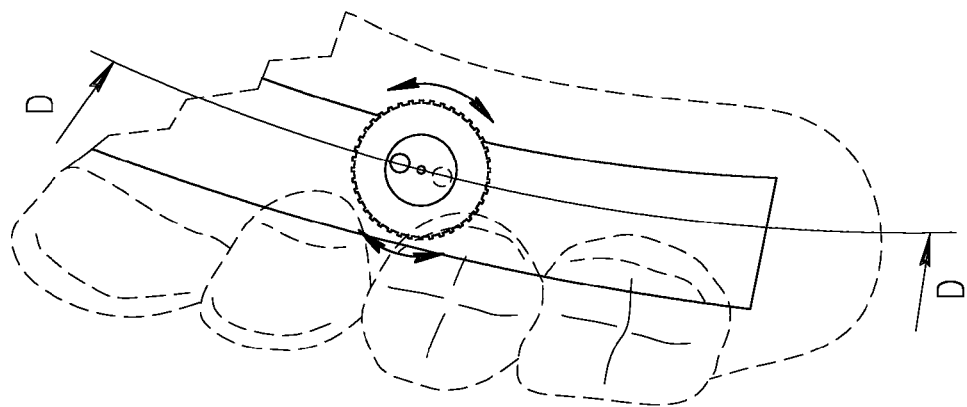
FIG. 22A is a schematic top representation of a modification of the locking arrangement illustrated in FIGS. 21A and 21B at a locked position.
Figure 21B:
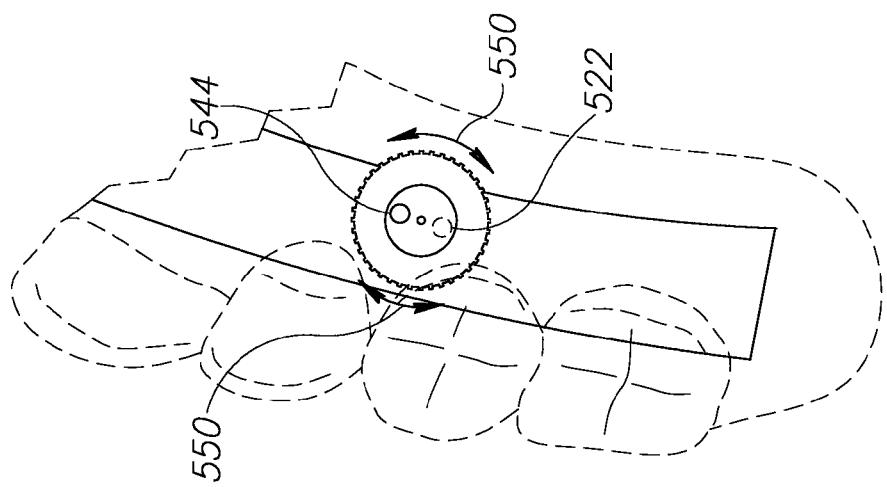
FIG. 21B illustrates the locking arrangement of FIG. 21A at its unlocked position.
Figure 21A:
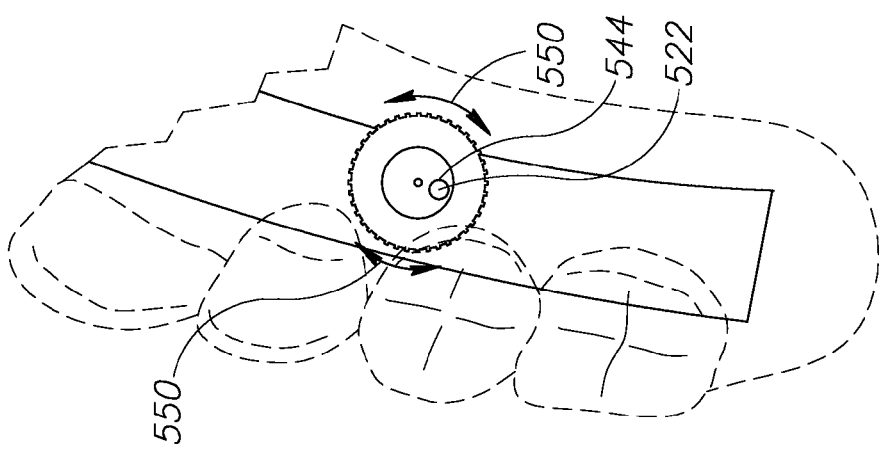
FIG. 21A illustrates a schematic top super position of the denture system fitted with a locking mechanism of the disclosed subject matter at a locked position.
Figure 23C:
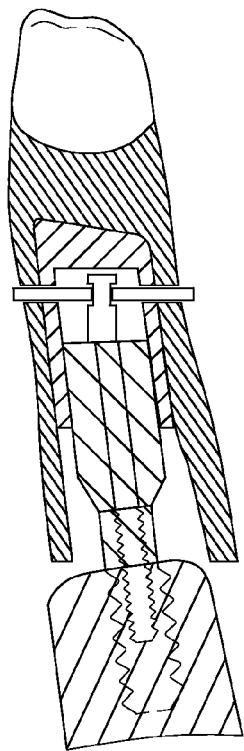
FIG. 23C is a schematic longitudinal section along the locking mechanism of FIG. 23A, illustrating the denture lockingly secured over the support beam.
Figure 23B:
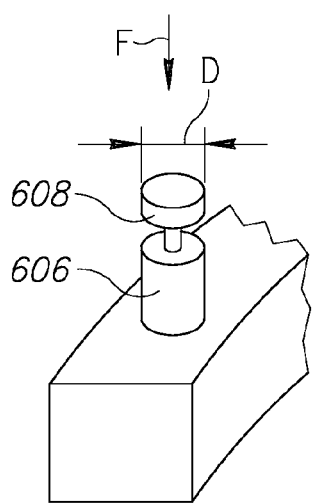
FIG. 23B is an enlargement of the encircled portion illustrated in FIG. 23A.
Figure 23A:
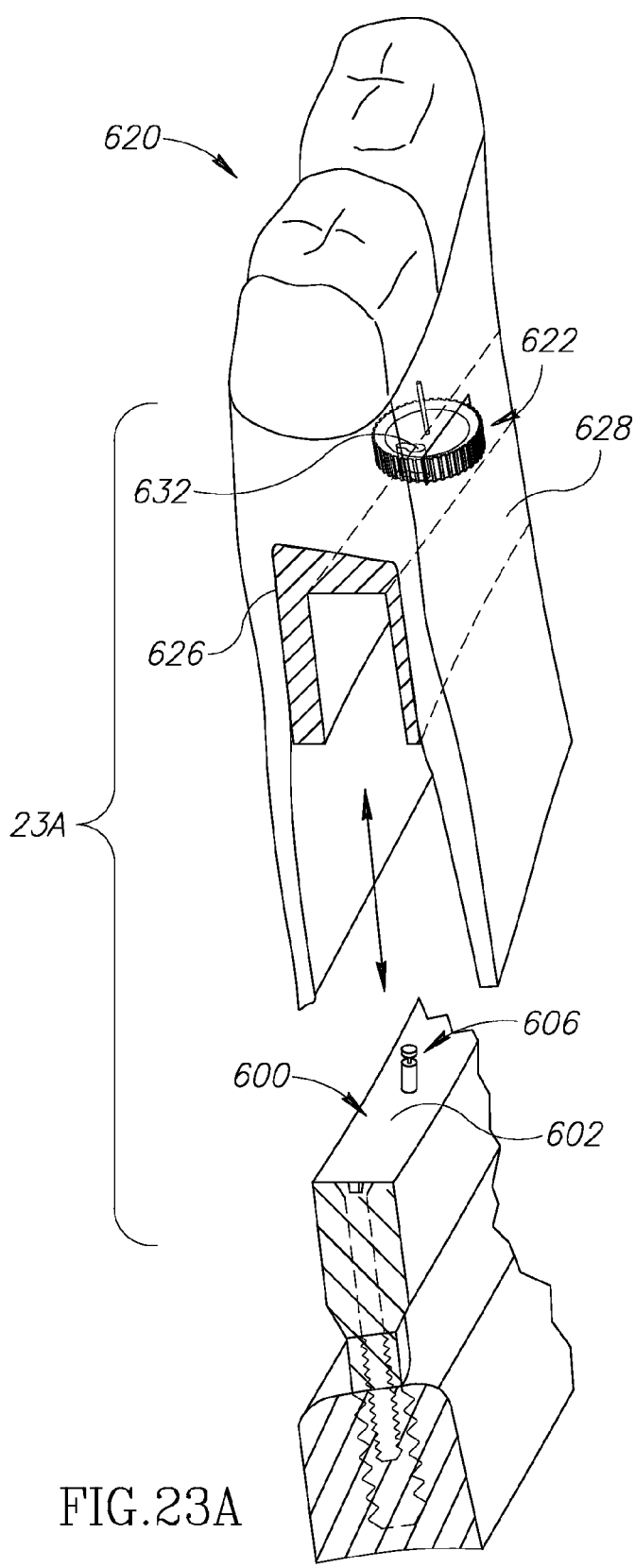
FIG. 23A is a perspective portion of a locking arrangement in accordance with a different example of the present disclosed subject matter.
Figure 23D:
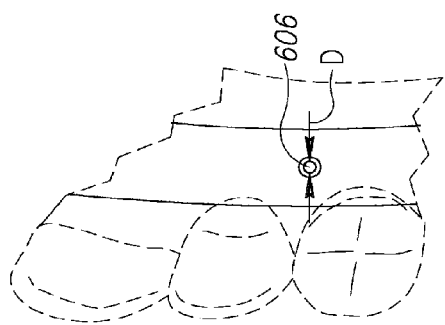
FIG. 23D is a top view of the support beam taken in direction of arrow F in FIG. 23B.
Figure 23E:
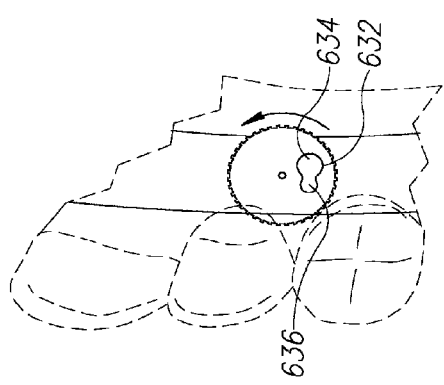
FIG. 23E is a schematic top view of the denture of FIG. 23A exemplifying the locking arrangement.

In FIGS. 22A and 22B there is illustrated a modification of the example disclosed in connection with FIGS. 20A-20C and 21A-21D, wherein the support beam is configured with a single magnet as illustrated in the previous example whilst the personalized denture 560 is configured with a disk-like manipulating member 562 fitted with two magnets 564 and 566, the former oriented as in the previous example namely with its south (S) pole facing downwards and its north (N) pole facing upwards, and the latter magnet 566 extending with its north (N) pole facing downwards and its south (S) pole facing upwards.

The arrangement is such that at a first orientation of the manipulator attraction forces extend between the first magnet 522 of the support beam and the second magnet 566 of the personalized denture, whilst unlocking the locking mechanism is facilitated by rotating the manipulator 562 to a position wherein the magnet 564 extends above the first magnet 522, giving rise to rejection forces therebetween, facilitating in easy extracting and removal of the denture.

Turning now to FIGS. 23A-23E there is illustrated a locking mechanism according to yet a different configuration wherein the support beam 600 is of the type disclosed hereinbefore and comprises at its top, substantially flat surface 602 one or more upwardly projecting locking studs 606 configured with a locking recess 608.

The personalized denture 620 is configured with a disk-like manipulator 622 projecting from either or both the lingual surface 626 or labial surface 628 and rotatable about an axis substantially parallel to a longitudinal axis of the locking stud 606, said locking manipulator is configured with a locking aperture 632 having a wide portion 634 and a narrow portion 636 (FIG. 23E) wherein the wide portion 634 is at least as wide as the diameter D of the locking stud 606 and the narrow portion 636 is as narrow as the recessed portion d (FIG. 23B) of the locking stud 606.

Figure 24A:
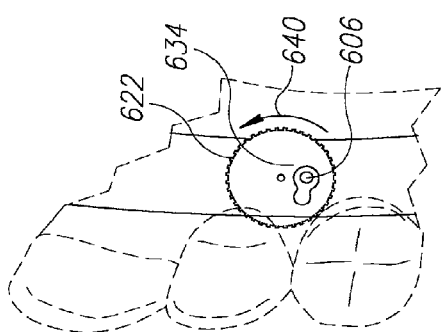
FIG. 24A is a super imposed schematic illustration illustrating the locking arrangement at its open position.
Figure 24B:
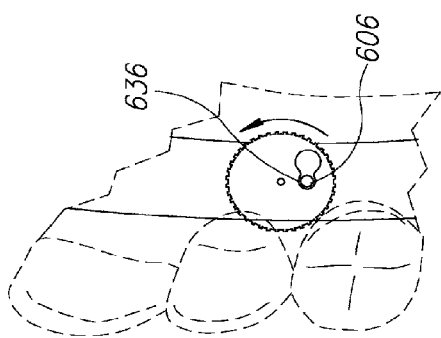
FIG. 24B illustrates the locking mechanism at its locked position.

At the unlocked position the personalized denture 620 is positioned over the support beam 600 allowing the stud 606 to project into the wide opening 634 of the opening 632 (FIG. 24A) thereby obtaining proper positioning and seating of the personalized denture over the support beam. Locking takes place by rotation of the manipulating member 622 in direction of arrow 640 (FIG. 24A) whereby the narrow portion 636 of the locking opening 632 lockingly arrests the locking recess 608 of the locking stud 606, thus preventing unintentional displacement of the denture from the support beam and eliminating any forces.

It is appreciated that according to any of the above disclosed locking mechanisms, at the locked position, the locking mechanism does not bear any loads but rather, the super-structure of the personalized denture snugly bears over the support beam with substantially zero tolerances therebetween.

While there have been shown several examples of the disclosed subject matter, it is to be understood that many changes may be made therein without departing from the spirit of the invention, mutatis mutandis. For example, the denture system according to the disclosed subject matter may be designed with a support beam configured with one or more positioning projections and one or more positioning grooves, and the super-structure be configured corresponding with one or more positioning grooved and one or more positioning projections, respectively.

The invention claimed is:

1. A removable denture system comprising:
a personalized support beam configured to be fixedly attached to an individual's jaw bone by a plurality of dental implants;
a personalized denture conforming with dental parameters of the individual and having fixedly integrated within a bottom surface thereof a super-structure cooperating with the support beam; and
a denture locking arrangement for securely locking and unlocking the denture to the support beam,
wherein the support beam or the super-structure comprises one or more positioning grooves extending parallel to a path of insert (POI) of the denture, and the super-structure or the support beam, respectively, comprise one or more corresponding laterally projecting positioning projections, each positioning projection configured to register with a corresponding positioning groove, and configured to provide a snug fit together,
wherein the support beam and super-structure are configured to eliminate movement between the super-structure and support beam when the super-structure of the denture is assembled to the support beam, and
wherein the one or more positioning grooves and the corresponding one or more positioning projections are configured on either or both a labial face and a lingual face of the super-structure and the support beam, respectively.

2. A removable denture system according to claim 1, wherein the one or more positioning grooves and/or the one or more positioning projections are configured with a cross-section tapering along the path of insert (POI).

3. A removable denture system according to claim 1, wherein the one or more positioning projections and the one or more positioning grooves comprise a funnel-like configuration providing an easy and correct positioning of the super-structure over the support beam.

4. A removable denture system according to claim 1, wherein one or more positioning grooves extend the entire height of the support beam or the super-structure.

5. A removable denture system according to claim 1, wherein the positioning projections are configured on the support beam, the super-structure follows the shape of the support beam, maintaining a thickness substantially conforming with a corresponding decrease of thickness of the personalized denture.

6. A removable denture system according to claim 1, wherein the one or more positioning grooves and the one or more positioning projections are configured for sliding engagement, with no movement therebetween.

7. A removable denture system according to claim 1, wherein the one or more positioning projections extend a height ranging between a full height to a portion of the height of the corresponding positioning grooves.

8. A removable denture system according to claim 1, wherein one of a lower surface of the super-structure or an upper surface of the support beam is configured with recesses or depressions and the other of the lower surface of the super-structure or an upper surface of the support beam is configured with corresponding protuberances or additional positioning projections in register with said recesses or depressions.

9. A removable denture system according to claim 1, wherein a top surface of the support beam, and respectively a lower surface of the super-structure comprises a flat portion.

10. A removable denture system according to claim 1, wherein a top surface of the support beam, and respectively a lower surface of the super-structure comprising one or more ridges.

11. A removable denture system according to claim 1, wherein side walls of the support beam, and respectively, side walls of the super-structure are substantially parallel to one another.

12. A removable denture system according to claim 1, wherein side walls of the support beam, and respectively, side walls of the super-structure are inclined with respect to one another at between 0° to 30°.

13. A removable denture system according to claim 1, wherein side wall surfaces of the super-structure cooperate with the respective walls of the support beam and all surfaces of the walls to provide the snug fit together, to eliminate any tolerances between the super-structure and support beam, to thereby ensure motionless fitting of the denture over the support beam and however facilitating for its easy mounting and removal, per demand.

14. The removable denture system according to claim 13, wherein the positioning protrusions and the positioning grooves are configured to provide the snug fit together.

15. The removable denture system according to claim 1, wherein the positioning protrusions and the positioning grooves are configured to provide the snug fit together.

16. A removable denture system comprising:
a personalized support beam configured to be fixedly attached to an individual's jaw bone by a plurality of dental implants;
a personalized denture conforming with dental parameters of the individual and having fixedly integrated within a bottom surface thereof a super-structure cooperating with the support beam; and
a denture locking arrangement for securely locking and unlocking the denture to the support beam,
wherein the support beam or the super-structure comprises one or more positioning grooves extending parallel to a path of insert (POI) of the denture, and the super-structure or the support beam, respectively, comprises one or more corresponding laterally projecting positioning projections, each positioning projection configured to register with a corresponding positioning groove and configured for snug fit there within when the super-structure is assembled to the support beam, contributing thereby to rigidity and grip of the super-structure over the support beam and easing guiding of the super-structure over the support beam,
wherein the one or more positioning grooves and/or the one or more positioning projections are configured with a cross-section tapering along the path of insert (POI), and
wherein the one or more positioning grooves and the corresponding one or more positioning projections are configured on either or both a labial face and a lingual face of the super-structure and the support beam, respectively.

17. The removable denture system according to claim 16, wherein the one or more positioning grooves and/or the one or more positioning projections are configured with a cross-section tapering along the path of insert (POI).

18. The removable denture system according to claim 16, wherein the one or more positioning projections and the one or more positioning grooves comprise a funnel-like configuration providing an easy and correct positioning of the super-structure over the support beam.

19. The removable denture system according to claim 16, wherein one of a lower surface of the super-structure or an upper surface of the support beam is configured with recesses or depressions and the other of the lower surface of the super-structure or an upper surface of the support beam is configured with corresponding protuberances or additional positioning projections in register with said recesses or depressions.

20. The removable denture system according to claim 16, wherein side wall surfaces of the super-structure follow and correspond with the shape of the respective walls of the support beam and all surfaces of said walls are in a snug fit, substantially eliminating any tolerances therebetween, to thereby ensure motionless fitting of the denture over the support beam and however facilitating for its easy mounting and removal, per demand.

21. A removable denture system comprising:
a personalized support beam configured to be fixedly attached to an individual's jaw bone by a plurality of dental implants;
a personalized denture conforming with dental parameters of the individual and having fixedly integrated within a bottom surface thereof a super-structure cooperating with the support beam; and
a denture locking arrangement for securely locking and unlocking the denture to the support beam,
wherein the support beam or the super-structure comprises one or more positioning grooves extending parallel to a path of insert (POI) of the denture, and the super-structure or the support beam, respectively, comprises one or more corresponding laterally projecting positioning projections, each positioning projection extending in register with a corresponding positioning groove and configured for snug fit there within when the super-structure is assembled to the support beam, contributing thereby to rigidity and grip of the super-structure over the support beam and easing guiding of the super-structure over the support beam,
wherein the one or more positioning projections and the one or more positioning grooves comprise a funnel-like configuration providing an easy and correct positioning of the super-structure over the support beam, and
wherein the one or more positioning grooves and the corresponding one or more positioning projections are configured on either or both a labial face and a lingual face of the super-structure and the support beam, respectively.

22. The removable denture system according to claim 21, wherein the one or more positioning grooves and/or the one or more positioning projections are configured with a cross-section tapering along the path of insert (POI).

23. The removable denture system according to claim 21, wherein the one or more positioning projections and the one or more positioning grooves comprise a funnel-like configuration providing an easy and correct positioning of the super-structure over the support beam.

24. The removable denture system according to claim 21, wherein one of a lower surface of the super-structure or an upper surface of the support beam is configured with recesses or depressions and the other of the lower surface of the super-structure or an upper surface of the support beam is configured with corresponding protuberances or additional positioning projections in register with said recesses or depressions.

25. The removable denture system according to claim 21, wherein side wall surfaces of the super-structure follow and correspond with the shape of the respective walls of the support beam and all surfaces of said walls are in a snug fit, substantially eliminating any tolerances therebetween, to thereby ensure motionless fitting of the denture over the support beam and however facilitating for its easy mounting and removal, per demand.

26. A removable denture system comprising:
a personalized support beam configured to be fixedly attached to an individual's jaw bone by a plurality of dental implants;
a personalized denture conforming with dental parameters of the individual and having fixedly integrated within a bottom surface thereof a super-structure cooperating with the support beam; and
a denture locking arrangement for securely locking and unlocking the denture to the support beam, wherein the support beam or the super-structure comprises one or more positioning grooves extending parallel to a path of insert (POI) of the denture, and the super-structure or the support beam, respectively, comprises one or more corresponding laterally projecting positioning projections, each positioning projection configured to register with a corresponding positioning groove and configured for snug fit there within when the super-structure is assembled to the support beam, contributing thereby to rigidity and grip of the super-structure over the support beam and easing guiding of the super-structure over the support beam, wherein the one or more positioning grooves and the corresponding one or more positioning projections are configured on either or both a labial face and a lingual face of the super-structure and the support beam, respectively; and wherein the one or more positioning grooves are multiple positioning grooves and the corresponding one or more positioning projections are multiple positioning projections.

27. The removable denture system according to claim 26, wherein the one or more positioning grooves and/or the one or more positioning projections are configured with a cross-section tapering along the path of insert (POI).

28. The removable denture system according to claim 26, wherein the one or more positioning projections and the one or more positioning grooves comprise a funnel-like configuration providing an easy and correct positioning of the super-structure over the support beam.

29. The removable denture system according to claim 26, wherein one of a lower surface of the super-structure or an upper surface of the support beam is configured with recesses or depressions and the other of the lower surface of the super-structure or an upper surface of the support beam is configured with corresponding protuberances or additional positioning projections in register with said recesses or depressions.

30. The removable denture system according to claim 26, wherein side wall surfaces of the super-structure follow and correspond with the shape of the respective walls of the support beam and all surfaces of said walls in a snug fit, substantially eliminating any tolerances therebetween, to thereby ensure motionless fitting of the denture over the support beam and however facilitating for its easy mounting and removal, per demand.

31. A removable denture system comprising:
a personalized support beam configured to be fixedly attached to an individual's jaw bone by a plurality of dental implants;
a personalized denture conforming with dental parameters of the individual and having fixedly integrated within a bottom surface thereof a super-structure cooperating with the support beam; and
a denture locking arrangement for securely locking and unlocking the denture to the support beam,
wherein the support beam or the super-structure comprises one or more positioning grooves extending parallel to a path of insert (POI) of the denture, and the super-structure or the support beam, respectively, comprises one or more corresponding laterally projecting positioning projections, each positioning projection configured to register with a corresponding positioning groove and configured for snug fit there within when the super-structure is assembled to the support beam, contributing thereby to rigidity and grip of the super-structure over the support beam and easing guiding of the super-structure over the support beam, wherein one of a lower surface of the super-structure or an upper surface of the support beam is configured with recesses or depressions and the other of the lower surface of the super-structure or an upper surface of the support beam is configured with corresponding protuberances or additional positioning projections in register with said recesses or depressions, and wherein the one or more positioning grooves and the corresponding one or more positioning projections are configured on either or both a labial face and a lingual face of the super-structure and the support beam, respectively.

32. The removable denture system according to claim 31, wherein the one or more positioning grooves and/or the one or more positioning projections are configured with a cross-section tapering along the path of insert (POI).

33. The removable denture system according to claim 31, wherein the one or more positioning projections and the one or more positioning grooves comprise a funnel-like configuration providing an easy and correct positioning of the super-structure over the support beam.

34. The removable denture system according to claim 31, wherein one of a lower surface of the super-structure or an upper surface of the support beam is configured with recesses or depressions and the other of the lower surface of the super-structure or an upper surface of the support beam is configured with corresponding protuberances or additional positioning projections in register with said recesses or depressions.

35. The removable denture system according to claim 31, wherein side wall surfaces of the super-structure follow and correspond with the shape of the respective walls of the support beam and all surfaces of said walls are in a snug fit, substantially eliminating any tolerances therebetween, to thereby ensure motionless fitting of the denture over the support beam and however facilitating for its easy mounting and removal, per demand.

36. A removable denture system comprising:
a personalized support beam configured to be fixedly attached to an individual's jaw bone by a plurality of dental implants, the support beam comprising one or more contact surfaces;
a personalized denture conforming with dental parameters of the individual and having fixedly integrated within a bottom surface thereof a super-structure cooperating with the support beam, the super-structure comprising one or more contact surfaces; and
a denture locking arrangement for securely locking and unlocking the denture to the support beam,
wherein the support beam or the super-structure comprises one or more positioning grooves extending parallel to a path of insert (POI) of the denture, and the super-structure or the support beam, respectively, comprises one or more corresponding positioning projections laterally projecting from the one or more contact surfaces of the superstructure or support beam, each positioning projection configured to register with a corresponding positioning groove and provide a snug fit there within when the super-structure is assembled to the support beam, enhancing rigidity and grip of the super-structure fitting over the support beam and easing guiding of the super-structure over the support beam, and
wherein the one or more positioning grooves and the corresponding one or more positioning projections are configured on either or both a labial face and a lingual face of the super-structure and the support beam, respectively.

37. The removable denture system according to claim 36, wherein the one or more positioning grooves and/or the one or more positioning projections are configured with a cross-section tapering along the path of insert (POI).

38. The removable denture system according to claim 36, wherein the one or more positioning projections and the one or more positioning grooves comprise a funnel-like configuration providing an easy and correct positioning of the super-structure over the support beam.

39. The removable denture system according to claim 36, wherein one of a lower surface of the super-structure or an upper surface of the support beam is configured with recesses or depressions and the other of the lower surface of the super-structure or an upper surface of the support beam is configured with corresponding protuberances or additional positioning projections in register with said recesses or depressions.

40. The removable denture system according to claim 36, wherein side wall surfaces of the super-structure follow and correspond with the shape of the respective walls of the support beam and all surfaces of said walls are in a snug fit, substantially eliminating any tolerances therebetween, to thereby ensure motionless fitting of the denture over the support beam and however facilitating for its easy mounting and removal, per demand.

41. A removable denture system comprising:
a personalized support beam configured to be fixedly attached to an individual's jaw bone by a plurality of dental implants, the support beam comprising side walls;
a personalized denture conforming with dental parameters of the individual and having fixedly integrated within a bottom surface thereof a super-structure cooperating with the support beam, the super-structure comprising side walls; and
a denture locking arrangement for securely locking and unlocking the denture to the support beam,
wherein the support beam or the super-structure comprises one or more positioning grooves located within the side walls of the support beam or located within the side wall of the super-structure, the positioning grooves extending parallel to a path of insert (POI) of the denture, and the super-structure or the support beam, respectively, comprises one or more positioning projections laterally projecting inwardly from the side walls of the superstructure or laterally projecting outwardly from the side walls of the support beam, each positioning projection configured to register with a corresponding positioning groove and provide a snug fit there within, enhancing rigidity and grip of the super-structure fitting over the support beam and easing guiding of the super-structure over the support beam, and
wherein the one or more positioning grooves and the corresponding one or more positioning projections are configured on either or both a labial face and a lingual face of the sidewalls of the super-structure and the support beam, respectively.

42. The removable denture system according to claim 41, wherein the one or more positioning grooves and/or the one or more positioning projections are configured with a cross-section tapering along the path of insert (POI).

43. The removable denture system according to claim 41, wherein the one or more positioning projections and the one or more positioning grooves comprise a funnel-like configuration providing an easy and correct positioning of the super-structure over the support beam.

44. The removable denture system according to claim 41, wherein one of a lower surface of the super-structure or an upper surface of the support beam is configured with recesses or depressions and the other of the lower surface of the super-structure or an upper surface of the support beam is configured with corresponding protuberances or additional positioning projections in register with said recesses or depressions.

45. The removable denture system according to claim 41, wherein side wall surfaces of the super-structure follow and correspond with the shape of the respective walls of the support beam and all surfaces of said walls are in a snug fit, substantially eliminating any tolerances therebetween, to thereby ensure motionless fitting of the denture over the support beam and however facilitating for its easy mounting and removal, per demand.

46. A removable denture system comprising:
a personalized support beam configured to be fixedly attached to an individual's jaw bone by a plurality of dental implants;
a personalized denture conforming with dental parameters of the individual and having fixedly integrated within a bottom surface thereof a super-structure cooperating with the support beam; and
a denture locking arrangement for securely locking and unlocking the denture to the support beam,
wherein the support beam or the super-structure comprises one or more positioning grooves extending parallel to a path of insert (POI) of the denture, and the super-structure or the support beam, respectively, comprise one or more corresponding laterally projecting positioning projections, each positioning projection configured to register with a corresponding positioning groove, and configured to provide a snug fit together,
wherein the support beam and super-structure are configured to eliminate movement between the super-structure and support beam when the super-structure of the denture is assembled to the support beam, and
wherein the one or more positioning projections and the one or more positioning grooves comprise a funnel-like configuration providing an easy and correct positioning of the super-structure over the support beam.

* * * * *